(12) United States Patent
King

(10) Patent No.: US 8,980,317 B2
(45) Date of Patent: Mar. 17, 2015

(54) METHODS AND COMPOSITIONS FOR TREATING INFECTIONS COMPRISING A LOCAL ANESTHETIC

(75) Inventor: Vanja Margareta King, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 872 days.

(21) Appl. No.: 12/614,711

(22) Filed: Nov. 9, 2009

(65) Prior Publication Data

US 2010/0160375 A1   Jun. 24, 2010

Related U.S. Application Data

(60) Provisional application No. 61/140,368, filed on Dec. 23, 2008.

(51) Int. Cl.
*A61K 31/445* (2006.01)
*A61M 19/00* (2006.01)
*A61K 9/00* (2006.01)
*A61K 9/06* (2006.01)
*A61K 9/70* (2006.01)

(52) U.S. Cl.
CPC ............. *A61K 31/445* (2013.01); *A61K 9/0024* (2013.01); *A61K 9/06* (2013.01); *A61K 9/7007* (2013.01)
USPC ............................ 424/468; 514/315; 424/426

(58) Field of Classification Search
CPC ..... A61K 31/445; A61K 9/0024; A61K 9/06; A61K 9/7007
USPC ................... 424/426, 468; 514/315
See application file for complete search history.

(56) References Cited

U.S. PATENT DOCUMENTS

| | | |
|---|---|---|
| 4,624,255 A | 11/1986 | Schenck et al. |
| 4,863,457 A | 9/1989 | Lee |
| 5,522,844 A | 6/1996 | Johnson |
| 5,626,838 A | 5/1997 | Cavanaugh, Jr. |
| 5,759,583 A | 6/1998 | Iwamoto et al. |
| 5,868,789 A | 2/1999 | Huebner |
| 5,942,241 A | 8/1999 | Chasin et al. |
| 6,069,129 A | 5/2000 | Sandberg et al. |
| 6,179,862 B1 | 1/2001 | Sawhney |
| 6,248,345 B1 | 6/2001 | Goldenheim et al. |
| 6,287,588 B1 | 9/2001 | Shih et al. |
| 6,326,020 B1 | 12/2001 | Kohane et al. |
| 6,331,311 B1 | 12/2001 | Brodbeck et al. |
| 6,428,804 B1 | 8/2002 | Suzuki et al. |
| 6,451,335 B1 * | 9/2002 | Goldenheim et al. ........ 424/426 |
| 6,461,631 B1 | 10/2002 | Dunn et al. |
| 6,524,607 B1 | 2/2003 | Goldenheim et al. |
| 6,534,081 B2 | 3/2003 | Goldenheim et al. |
| 6,589,549 B2 | 7/2003 | Shih et al. |

(Continued)

*Primary Examiner* — Savitha Rao
(74) *Attorney, Agent, or Firm* — Sorell Lenna & Schmidt LLP

(57) ABSTRACT

The present invention is directed to a drug depot useful for reducing, preventing or treating an infection in a patient in need of such treatment. The drug depot includes a polymer and a therapeutically effective amount of a local anesthetic or pharmaceutically acceptable salt thereof. The drug depot is administered at a site to reduce, prevent or treat an infection. The drug depot is capable of releasing (i) a bolus dose of the local anesthetic or pharmaceutically acceptable salt thereof at the site and (ii) a sustained release dose of an effective amount of the local anesthetic or pharmaceutically acceptable salt thereof over a period of at least 4 days at the site.

14 Claims, 8 Drawing Sheets

(56) References Cited

U.S. PATENT DOCUMENTS

| | | |
|---|---|---|
| 6,630,155 B1 | 10/2003 | Chandrashekar et al. |
| 6,632,457 B1 | 10/2003 | Sawhney |
| 6,756,058 B2 | 6/2004 | Brubaker et al. |
| 6,773,714 B2 | 8/2004 | Dunn et al. |
| 6,921,541 B2 | 7/2005 | Chasin et al. |
| 6,974,462 B2 | 12/2005 | Sater |
| 7,144,412 B2 | 12/2006 | Wolf et al. |
| 7,166,570 B2 | 1/2007 | Hunter et al. |
| 7,220,281 B2 | 5/2007 | Lambrecht et al. |
| 7,229,441 B2 | 6/2007 | Trieu et al. |
| 7,235,043 B2 | 6/2007 | Gellman et al. |
| 7,287,983 B2 | 10/2007 | Ilan |
| 7,318,840 B2 | 1/2008 | McKay |
| 7,329,259 B2 | 2/2008 | Cragg |
| 7,361,168 B2 | 4/2008 | Makower et al. |
| 7,367,978 B2 | 5/2008 | Drewry et al. |
| 2002/0009454 A1 | 1/2002 | Boone et al. |
| 2002/0090398 A1 | 7/2002 | Dunn et al. |
| 2003/0224033 A1 | 12/2003 | Li et al. |
| 2006/0106361 A1 | 5/2006 | Muni et al. |
| 2006/0148903 A1 | 7/2006 | Burch et al. |
| 2006/0189944 A1 | 8/2006 | Campbell et al. |
| 2007/0156180 A1 | 7/2007 | Jaax et al. |
| 2007/0185497 A1 | 8/2007 | Cauthen et al. |
| 2007/0202074 A1 | 8/2007 | Shalaby |
| 2007/0243225 A1 | 10/2007 | McKay |
| 2007/0243228 A1 | 10/2007 | McKay |
| 2008/0091207 A1 | 4/2008 | Truckai et al. |
| 2009/0263441 A1* | 10/2009 | McKay .................. 424/422 |

* cited by examiner

METHODS AND COMPOSITIONS FOR TREATING INFECTIONS COMPRISING A LOCAL ANESTHETIC

This application claims the benefit of the filing date of U.S. Provisional Application No. 61/140,368 filed Dec. 23, 2008 and entitled "Methods and Compositions for Treating Infections Comprising a Local Anesthetic," which is hereby incorporated by reference thereto.

BACKGROUND

Every year, lives are lost because of the spread of infections. Infections result from the body's inability to fight off foreign microorganisms or pathogens that may cause damage or disease if left untreated. The infecting organism or pathogen can be a bacteria, virus, fungus or some other parasite. The infecting organism or pathogen seeks to utilize the host's resources to multiply (usually at the expense of the host) or colonize. The infecting organism or pathogen interferes with the normal functioning of the host and can lead to chronic wounds, gangrene, loss of an infected limb, death, etc.

There are many common infections and some very rare ones, all with varying causes and treatments. Common bacterial infections include strep throat, tuberculosis, urinary tract infections and microbial infections such as *E. coli* or *Staphylococcus aureus*. Bacterial infections are generally treated with an antibiotic specifically chosen to destroy the infectious bacteria and delivered systemically, however, antibiotics are sometimes not effective. In addition, systemically delivered antibiotics may result in adverse side effects.

Common viral infections include a cold and influenza. Viral and bacterial infections differ in that viral infections are caused by viruses which are smaller than a bacterium or fungus. When a virus infects healthy cells, it prevents the cells from doing their job and causes sickness. Viruses usually infect a specific type of cell which causes viral infections to affect certain parts of the body. Viral infections in some cases can be treated with antiviral drugs to stop the virus from replication, however, antiviral drugs are not always effective at preventing or stopping replication of the virus. Antibiotics are not effective against viral infections. As such, viral infections must generally run a natural course and be fought off by the body. However, the body sometimes has trouble fighting off the virus and the virus could promote subsequent infection by a bacterium or fungus.

Common fungal infections include ringworm, Athlete's foot and vaginal yeast infections. Fungal infections are caused by a fungus that has either been transmitted through contact or has grown as a result of certain conditions of the body. Fungal infections are treated with anti-fungal medications that may be applied as a cream or taken orally, however, these medications are also sometimes not effective and can result in serious adverse effects.

Infections can occur in many ways including during or following surgery and the implications can be very serious. Antibiotics have been used prior to and after surgery to treat infections, however, as stated above, antibiotics are not always effective and if the pathogen is not bacterial, the antibiotic will not be effective. In addition, if an infection occurs during surgery, a systemically administered antibiotic may not be effective quickly enough and a physician may need to access the site of infection to try to treat the infection.

Anesthetics are generally a class of drugs or agents that produce a local or general loss of sensation, including pain, and therefore are useful in surgery and dentistry. Local anesthetics are drugs or agents that cause reversible local anesthesia and a loss of nociception. Local anesthetics act mainly by reversibly binding to and inactivating sodium channels thereby inhibiting sodium influx through sodium-specific ion channels in the neuronal cell membrane. Sodium influx through these channels is necessary for the depolarization of nerve cell membranes and subsequent propagation of impulses along the course of the nerve. When a nerve loses depolarization and capacity to propagate an impulse, the individual loses sensation in the area supplied by the nerve. Local anesthetics are typically known for infiltration, epidural block and spinal anesthesia. Local anesthetics are not known for treating or preventing infections.

One local anesthetic that is known to the medical profession is bupivacaine, which is widely recognized as a local anesthetic for infiltration, nerve block, epidural and intrathecal administration. In general, bupivacaine, also referred to as 1-butyl-N-(2,6-dimethylphenyl)piperidine-2-carboxamide ($C_{18}H_{28}N_2O$) may be represented by the following structure:

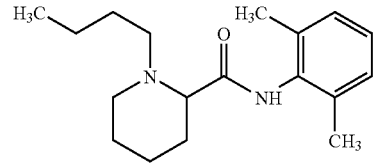 [SMILES: CCCCN1CCCCC1C(=O)Nc1c(C)cccc1C]

Bupivacaine has not been used nor known for treating or preventing infections. Rather, bupivacaine is often administered by epidural injection before total hip arthroplasty or injected to surgical wound sites to reduce pain after a surgery.

As the presently available treatments for several types of infections are sometimes not effective and cause undesirable side effects, there exists a need to prevent, treat or reduce infections using a medication that causes minimum or no side effects. New compositions comprising a local anesthetic are provided that effectively prevent, treat or reduce infections while causing minimum or no side effects.

SUMMARY

New compositions and methods are provided that effectively prevent, treat or reduce infections. The compositions and methods prevent, treat or reduce infections via a single drug depot or multiple drug depots. The compositions and methods allow accurate and precise administration of the drug depot(s) including an analgesic with minimal physical and psychological trauma to a patient. The drug depot(s) can be easily delivered to the target site (e.g., wound site, abdomen, synovial joint, at or near the spinal column, etc.) and treat infections for at least 4 to 10 days. In this way, accurate and precise administration of the drug depot(s) in a minimally invasive procedure can be accomplished.

In one embodiment, a drug depot useful for reducing, preventing or treating an infection in a patient in need of such treatment is provided. The drug depot comprises a therapeutically effective amount of an analgesic, local anesthetic or pharmaceutically acceptable salt thereof and the depot is administered at a site to reduce, prevent or treat an infection. The drug depot is capable of releasing an effective amount of the analgesic, local anesthetic or pharmaceutically acceptable salt thereof over a period of at least 4 days. The drug depot in this embodiment may be capable of releasing (i) a bolus dose of the analgesic, local anesthetic or pharmaceutically acceptable salt thereof at the site to reduce, prevent or treat an infection and (ii) a sustained release dose of an effective amount of the analgesic, local anesthetic or pharmaceutically acceptable salt thereof over a period of at least 4 days at the site to treat, reduce or prevent the infection. The bolus dose provides immediate relief to an existing infection followed by continuous treatment during at least 4 days. The drug depot may comprise a polymer. The drug depot can be a ribbon-like strip or fiber that releases the analgesic or local anesthetic over the period of at least 4 days. The drug depot can also be a gel formulation that releases the analgesic or local anesthetic over the period of at least 4 days.

In another embodiment, a method of making a drug depot is provided. The method comprises combining a biocompatible polymer and a therapeutically effective amount of local anesthetic or pharmaceutically acceptable salt thereof and forming the drug depot from the combination.

In yet another embodiment, a method of treating or preventing infections in a patient in need of such treatment is provided. The method comprises administering one or more biodegradable drug depots comprising a therapeutically effective amount of an analgesic, local anesthetic or pharmaceutically acceptable salt thereof to a target site, wherein the drug depot releases an effective amount of the analgesic, local anesthetic or pharmaceutically acceptable salt thereof over a period of at least 4 days. The drug depot may be capable of releasing (i) a bolus dose of the analgesic, local anesthetic or pharmaceutically acceptable salt thereof at a site and (ii) a sustained release dose of an effective amount of the analgesic, local anesthetic or pharmaceutically acceptable salt thereof over a period of at least 4 days at the site. The bolus dose provides immediate relief to an existing infection followed by continuous treatment during at least 4 days. The drug depot may comprise a polymer. The drug depot can be a ribbon-like strip that releases the analgesic or local anesthetic over the period of at least 4 days. The drug depot can also be a gel formulation that releases the analgesic or local anesthetic over the period of at least 4 days.

In still yet another embodiment, a drug depot useful for reducing, preventing or treating an infection in a patient in need of such treatment is provided. The drug depot comprises a therapeutically effective amount of bupivacaine or pharmaceutically acceptable salt thereof and a polymer. The depot is administered at a target site to reduce, prevent or treat an infection. The depot is capable of releasing (i) about 2% to about 50% of the bupivacaine or pharmaceutically acceptable salt thereof relative to a total amount of the bupivacaine or pharmaceutically acceptable salt thereof loaded in the drug depot over a first period of up to 48 hours, a first period of up to 24 hours, or a first period of about 24 to 48 hours and (ii) about 50% to about 98% of the bupivacaine or pharmaceutically acceptable salt thereof relative to a total amount of the bupivacaine or pharmaceutically acceptable salt thereof loaded in the drug depot over a subsequent period of up to 3 to 30 days, 2 to 10 days or 3 to 10 days. In various embodiments, when the first period is up to 24 hours or about 24 to 48 hours, the depot is capable of releasing about 2% to about 40% of the bupivacaine or pharmaceutically acceptable salt thereof.

In another embodiment, a drug depot for reducing, preventing or treating an infection in a patient in need of such treatment is provided. The drug depot comprises: (i) bupivacaine or pharmaceutically acceptable salt thereof at an amount of about 30 wt. % to about 90 wt. % of the drug depot; and (ii) at least one biodegradable material. The depot is capable of releasing an initial bolus dose of bupivacaine or pharmaceutically acceptable salt thereof at a site, and the depot is capable of releasing a sustained release dose of an effective amount of bupivacaine or pharmaceutically acceptable salt thereof over a subsequent period of at least 4 days, 4 to 30 days or 4 to 10 days. The bolus dose provides immediate relief to an existing infection followed by continuous treatment during the subsequent period. The drug depot is capable of releasing about 40% to about 70% of the bupivacaine or pharmaceutically acceptable salt thereof relative to a total amount of bupivacaine loaded in the drug depot over the sustained release period of at least 4 days, 4 to 30 days or 4 to 10 days after the drug depot is administered. The biodegradable material comprises one or more of poly(lactide-co-glycolide), polylactide, polyglycolide, polyorthoester, D-lactide, D,L-lactide, poly(D,L-lactide), L-lactide, poly(D,L-lactide-co-caprolactone), poly(D,L-lactide-co-glycolide-co-caprolactone), polycaprolactone or a combination thereof. In various embodiments, the biodegradable material comprises a polymer comprising poly(lactic-co-glycolic acid) or poly(orthoester) or both. In some embodiments, the biodegradable material comprises a polymer comprising poly(lactic-co-glycolic acid) wherein the poly(lactic-co-glycolic acid) comprises a mixture of polyglycolide and polylactide. The polymer can comprise more polylactide than polyglycolide.

In still another embodiment, the drug depot comprises an analgesic, a polymer and further an excipient. The drug depot may comprise an analgesic in an amount of about 30 to about 90 weight percent (wt. %), about 10 to about 80 wt. % of a polymer and about 0.5 to about 20 wt. % of an excipient. For example, the drug depot can include a local anesthetic at an amount of about 30 to about 90 wt. % of the drug depot, about 10 to about 80 wt. % PLGA and about 0.5 to about 20 wt. % mPEG.

In various embodiments, the analgesic may be a local anesthetic or a pharmaceutically acceptable salt thereof and the local anesthetic may be at least one of bupivacaine, ropivacaine, mepivacaine, etidocaine, levobupivacaine, trimecaine, carticaine or articaine. Bupivacaine may be in the form of a salt and/or in the form of a base. The local anesthetic or pharmaceutically acceptable salt thereof may be encapsulated in a plurality of depots comprising microparticles, microspheres, microcapsules, and/or microfibers suspended in a gel.

The drug depot in various embodiments is capable of releasing an effective amount of the analgesic, local anesthetic or pharmaceutically acceptable salt thereof over a period of at least 4 days. For example, the drug depot may release about 40% to about 70% of the analgesic, local anesthetic or pharmaceutically acceptable salt thereof relative to a total amount of the analgesic or local anesthetic loaded in the drug depot over a period of 4 to 10 days after the drug depot is administered to a target site. The analgesic or local anesthetic is released in an amount between 50 and 800 mg per day during this period of 4 to 10 days. The drug depot, though, is capable of releasing an effective amount of the analgesic, local anesthetic or pharmaceutically acceptable salt thereof over a much greater period, e.g., at least 7 days and in the range of 7 to 30 days, after the drug depot is administered to the site.

The polymer in various embodiments comprises one or more of poly(lactide-co-glycolide), polylactide, polyglycolide, polyorthoester, D-lactide, D,L-lactide, poly(D,L-lactide), L-lactide, poly(D,L-lactide-co-caprolactone), poly(D,L-lactide-co-glycolide-co-caprolactone), polycaprolactone or a combination thereof. The polymer(s) may be biodegradable. Further, if the polymer(s) are biodegradable, the polymer(s) may be capable of degrading or degrade in 30 days or less after the drug depot is administered at a site.

The target site can be a wound site, a muscle, a ligament, a tendon, cartilage, a spinal disc, the spinal foraminal space near the spinal nerve root, a facet or synovial joint, or the spinal canal.

The infection may result or be associated with hernia repair, orthopedic or spine surgery or a combination thereof. The surgery may be arthroscopic surgery, an excision of a mass, hernia repair, spinal fusion, thoracic, cervical, or lumbar surgery, pelvic surgery or a combination thereof.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

In part, other aspects, features, benefits and advantages of the embodiments will be apparent with regard to the following description, appended claims and accompanying drawings where:

Figure 1:
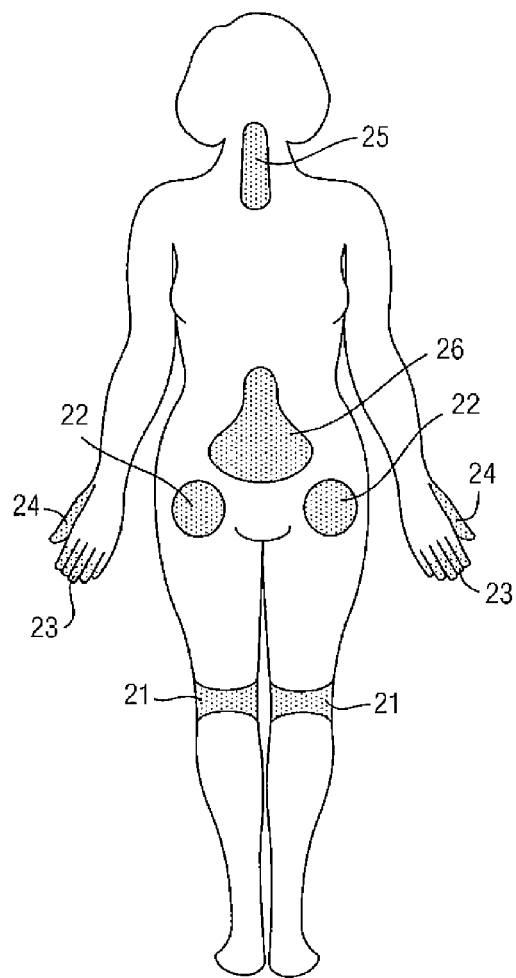
FIG. 1 illustrates a number of common locations within a patient that may be sites where surgery is conducted and locations where the drug depot containing an analgesic or local anesthetic can be administered thereto.

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

It is noted that, as used in this specification and the appended claims, the singular forms "a," "an," and "the," include plural referents unless expressly and unequivocally limited to one referent. Thus, for example, reference to "a drug depot" includes one, two, three or more drug depots.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents, which may be included within the invention as defined by the appended claims.

The headings below are not meant to limit the disclosure in any way; embodiments under any one heading may be used in conjunction with embodiments under any other heading.

New compositions and methods are provided that effectively prevent, treat or reduce an infection. The compositions and methods prevent, treat or reduce infections by administration of a single drug depot or multiple drug depots. The compositions and methods allow accurate and precise administration of the drug depot(s) including an analgesic such as bupivacaine with minimal physical and psychological trauma to a patient. The drug depot(s) can be easily delivered to the target site (e.g., wound site, abdomen, synovial joint, at or near the spinal column, etc.) and alleviate and/or treat an infection for at least 4 to 10 days. In this way, accurate and precise administration of the drug depot(s) in a minimally invasive procedure can be accomplished.

Bupivacaine

Bupivacaine or another local anesthetic may be contained in a drug depot. A drug depot comprises a physical structure to facilitate administration and retention in a desired site (e.g., a wound site, a synovial joint, a disc space, a spinal canal, abdominal area, a tissue of the patient, etc.). The drug depot also comprises the drug. The term "drug" as used herein is generally meant to refer to any substance that alters the physiology of a patient. The term "drug" may be used interchangeably herein with the terms "therapeutic agent", "therapeutically effective amount", and "active pharmaceutical ingredient" or "API". It will be understood that a "drug" formulation may include more than one therapeutic agent, wherein exemplary combinations of therapeutic agents include a combination of two or more drugs. The drug depot provides a concentration gradient of the therapeutic agent for delivery to the site. In various embodiments, the drug depot provides an optimal drug concentration gradient of the therapeutic agent at a distance of up to about 1 cm to about 10 cm from the implant site.

A "therapeutically effective amount" or "effective amount" is such that when administered, the drug results in alteration of the biological activity, such as, for example, inhibition of an infection, reduction or alleviation of an infection, improvement in the condition, etc. In various embodiments, the therapeutically effective amount of bupivacaine comprises from about 0.5 mg to 1,000 mg/day. In some embodiments, the therapeutically effective amount of bupivacaine comprises from about 0.1 mg to 800 mg of bupivacaine per day. In some embodiments, the therapeutically effective amount of bupivacaine comprises from about 50 mg to 800 mg of bupivacaine per day or from about 200 mg to 800 mg of bupivacaine per day. In some embodiments, the therapeutically effective amount of bupivacaine comprises about 0.5 mg, 100 mg, 200 mg, 300 mg, 400 mg, 500 mg, 600 mg, 700 mg, 800 mg, 900 mg, or 1,000 mg of bupivacaine per day and all subranges therebetween. In some embodiments, the therapeutically effective amount of bupivacaine comprises 0.5 mg, 0.6 mg, 0.7 mg, 0.8 mg, 0.9 mg, 1 mg, 1.1 mg, 1.2 mg, 1.3 mg, 1.4 mg, 1.5 mg, 1.6 mg, 1.7 mg, 1.8 mg, 1.9 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 30 mg, 35 mg, or 40 mg of bupivacaine per day. In one embodiment, the dosage to a human is between 400 mg and 600 mg of bupivacaine per day. It will be understood that the dosage administered to a patient can be as a single depot or multiple depots depending upon a variety of factors, including the drug's administered pharmacokinetic properties, the route of administration, patient conditions and characteristics (sex, age, body weight, health, size, etc.), extent of symptoms, concurrent treatments, frequency of treatment and the effect desired. For example, lower daily doses of bupivacaine may be needed when there is concurrent treatment.

In various embodiments, a therapeutically effective amount of bupivacaine is provided to inhibit, treat and/or prevent an infection. In general, the chemical name of bupivacaine is 1-butyl-N-(2,6-dimethylphenyl)piperidine-2-carboxamide. Bupivacaine has a molecular weight of 288.43 and exhibits the following general structure:

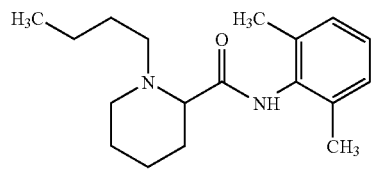 [SMILES: CCCCN1CCCCC1C(=O)Nc1c(C)cccc1C]

Bupivacaine includes, but is not limited to, (+/−)-1-butyl-N-(2,6-dimethylphenyl)piperidine-2-carboxamide or pharmaceutically acceptable non-toxic esters or salts thereof. Bupivacaine includes the racemic mixtures ((+)-R and (−)-S enantiomers) or each of the dextro and levo isomers of bupivacaine individually. Bupivacaine includes the free acid as well as any other pharmaceutically acceptable salt of any one of the foregoing. Bupivacaine may also be pegylated for long acting activity.

Pharmaceutically acceptable esters of bupivacaine include but are not limited to, alkyl esters derived from hydrocarbons of branched or straight chain having one to about 12 carbon atoms. Examples of such esters are methyl, ethyl, propyl, isopropyl, butyl, t-butyl, isoamyl, pentyl, isopentyl, hexyl, octyl, nonyl, isodecyl, 6-methyldecyl or dodecyl esters.

Pharmaceutically acceptable salts of bupivacaine include salts derived from either inorganic or organic bases. Salts derived from inorganic bases include, but are not limited to, sodium, potassium, lithium, ammonium, calcium, magnesium, ferrous, zinc, copper, manganese, aluminum, ferric, manganic salts or the like. Salts derived from pharmaceutically acceptable organic non-toxic bases include, but are not limited to, salts of primary, secondary, or tertiary amines, substituted amines including naturally occurring substituted amines or cyclic amines or basic ion exchange resins, such as isopropylamine, trimethylamine, diethylamine, triethylamine, tripropylamine, ethanolamine, 2-dimethylaminoethanol, 2-diethylaminoethanol, tromethamine, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins or the like.

In addition to bupivacaine, the drug depot may comprise one or more additional therapeutic agents. Examples of therapeutic agents include, those that are direct- and local-acting modulators of pro-inflammatory cytokines such as TNF-α and IL-1 including, but not limited to, soluble tumor necrosis factor α receptors, any pegylated soluble tumor necrosis factor α receptor, monoclonal or polyclonal antibodies or antibody fragments or combinations thereof. Examples of suitable therapeutic agents include receptor antagonists, molecules that compete with the receptor for binding to the target molecule, antisense polynucleotides, and inhibitors of transcription of the DNA encoding the target protein. Suitable examples include but are not limited to Adalimumab, Infliximab, Etanercept, Pegsunercept (PEG sTNF-R1), sTNF-R1, CDP-870, CDP-571, CNI-1493, RDP58, ISIS 104838, 1→3-β-D-glucans, Lenercept, PEG-sTNFRII Fc Mutein, D2E7, Afelimomab, and combinations thereof. In other embodiments, a therapeutic agent includes metalloprotease inhibitors, glutamate antagonists, glial cell-derived neurotropic factors (GDNF), B2 receptor antagonists, Substance P receptor (NK1) antagonists such as capsaicin and civamide, downstream regulatory element antagonistic modulator (DREAM), iNOS, inhibitors of tetrodotoxin (TTX)-resistant Na+-channel receptor subtypes PN3 and SNS2, inhibitors of interleukins such as IL-1, IL-6 and IL-8, and anti-inflammatory cytokines, TNF binding protein, onercept (r-hTBP-1), recombinant adeno-associated viral (rAAV) vectors encoding inhibitors, enhancers, potentiators, or neutralizers, antibodies, including but not limited to naturally occurring or synthetic, double-chain, single-chain, or fragments thereof. For example, suitable therapeutic agents include molecules that are based on single chain antibodies called Nanobodies™ (Ablynx, Ghent Belgium), which are defined as the smallest functional fragment of a naturally occurring, single-domain antibody. Alternatively, therapeutic agents include, agents that effect kinases and/or inhibit cell signaling mitogen-activated protein kinases (MAPK), p38 MAPK, Src or protein tyrosine kinase (PTK). Therapeutic agents include, kinase inhibitors such as, for example, Gleevec, Herceptin, Iressa, imatinib (STI571), herbimycin A, tyrphostin 47, erbstatin, genistein, staurosporine, PD98059, SB203580, CNI-1493, VX-50/702 (Vertex/Kissei), SB203580, BIRB 796 (Boehringer Ingelheim), Glaxo P38 MAP Kinase inhibitor, RWJ67657 (J&J), UO126, Gd, SCIO-469 (Scios), RO3201195 (Roche), Semipimod (Cytokine Pharma-Sciences), or derivatives thereof.

Therapeutic agents, in various embodiments, block the transcription or translation of TNF-α or other proteins in the inflammation cascade. Suitable therapeutic agents include, but are not limited to, integrin antagonists, alpha-4 beta-7 integrin antagonists, cell adhesion inhibitors, interferon gamma antagonists, CTLA4-Ig agonists/antagonists (BMS-188667), CD40 ligand antagonists, Humanized anti-IL-6 mAb (MRA, Tocilizumab, Chugai), HMGB-1 mAb (Critical Therapeutics Inc.), anti-IL2R antibodies (daclizumab, basilicimab), ABX (anti IL-8 antibodies), recombinant human IL-10, or HuMax IL-15 (anti-IL 15 antibodies).

Other suitable therapeutic agents include IL-1 inhibitors, such as Kineret® (anakinra) which is a recombinant, non-glycosylated form of the human interleukin-1 receptor antagonist (IL-1Ra), or AMG 108, which is a monoclonal antibody that blocks the action of IL-1. Therapeutic agents also include excitatory amino acids such as glutamate and aspartate, antagonists or inhibitors of glutamate binding to NMDA receptors, AMPA receptors, and/or kainate receptors. Interleukin-1 receptor antagonists, thalidomide (a TNF-α release inhibitor), thalidomide analogues (which reduce TNF-α production by macrophages), bone morphogenetic protein (BMP) type 2 and BMP-4 (inhibitors of caspase 8, a TNF-α activator), quinapril (an inhibitor of angiotensin II, which upregulates TNF-α), interferons such as IL-11 (which modulate TNF-α receptor expression), and aurin-tricarboxylic acid (which inhibits TNF-α), for example, may also be useful as therapeutic agents for reducing inflammation. It is contemplated that where desirable a pegylated form of the above may be used. Examples of other therapeutic agents include NF kappa B inhibitors such as glucocorticoids, clonidine; antioxidants, such as dithiocarbamate, and other compounds, such as, for example, sulfasalazine.

Specific examples of therapeutic agents suitable for use include, but are not limited to, an anti-inflammatory agent, analgesic agent, or osteoinductive growth factor or a combination thereof. Anti-inflammatory agents include, but are not limited to, salicylates, diflunisal, sulfasalazine, indomethacin, ibuprofen, naproxen, tolmetin, diclofenac, ketoprofen, fenamates (mefenamic acid, meclofenamic acid), enolic acids (piroxicam, meloxicam), nabumetone, celecoxib, etodolac, nimesulide, apazone, gold, sulindac or tepoxalin; antioxidants, such as dithiocarbamate, and other compounds such as sulfasalazine[2-hydroxy-5-[-4-[C2-pyridinylamino)sulfonyl]azo]benzoic acid], steroids, such as fluocinolone, cortisol, cortisone, hydrocortisone, fludrocortisone, prednisone, prednisolone, methylprednisolone, triamcinolone, betamethasone, dexamethasone, beclomethasone, fluticasone or a combination thereof.

Suitable anabolic growth or anti-catabolic growth factors include, but are not limited to, a bone morphogenetic protein, a growth differentiation factor, a LIM mineralization protein, CDMP or progenitor cells or a combination thereof.

Additional analgesic agents may also be included in the depot. Suitable analgesic agents include, but are not limited to, acetaminophen, lidocaine, opioid analgesics such as buprenorphine, butorphanol, dextromoramide, dezocine, dextropropoxyphene, diamorphine, fentanyl, alfentanil, sufentanil, hydrocodone, hydromorphone, ketobemidone, levomethadyl, mepiridine, methadone, morphine, nalbuphine, opium, oxycodone, papaveretum, pentazocine, pethidine, phenoperidine, piritramide, dextropropoxyphene, remifentanil, tilidine, tramadol, codeine, dihydrocodeine, meptazinol, dezocine, eptazocine, flupirtine or a combination thereof.

Suitable analgesics also include agents with analgesic properties, such as for example, amitriptyline, carbamazepine, gabapentin, pregabalin, clonidine, or a combination thereof.

The depot may contain a muscle relaxant. Exemplary muscle relaxants include by way of example and not limitation, alcuronium chloride, atracurium besoylate, baclofen, carbolonium, carisoprodol, chlorphenesin carbamate, chlorzoxazone, cyclobenzaprine, dantrolene, decamethonium bromide, fazadinium, gallamine triethiodide, hexafluorenium, meladrazine, mephensin, metaxalone, methocarbamol, metocurine iodide, pancuronium, pridinol mesylate, styramate, suxamethonium, suxethonium, thiocolchicoside, tizanidine, tolperisone, tubocuarine, vecuronium, or combinations thereof.

The depot comprises the therapeutic agent or agents and may also contain other non-active ingredients. These non-active ingredients may have a multi-functional purpose including the carrying, stabilizing and controlling of the release of the therapeutic agent(s). The sustained release process, for example, may be by a solution-diffusion mechanism or it may be governed by an erosion-controlled process. Typically, the depot will be a solid or semi-solid formulation comprised of a biocompatible material, which can be biodegradable. The term "solid" is intended to mean a non-gel like material, while, "semi-solid" is intended to mean a gel like material that has some degree of flowability, thereby allowing the depot to bend and conform to the surrounding tissue requirements. The term "gel" is intended to mean a material that is soft and deformable at any point in its application to the surgical site.

In various embodiments, the depot material will be durable on or within the target site for a period of time similar to (for biodegradable components) or greater than (for non-biodegradable components) the planned period of drug delivery. For example, the depot material may have a melting point or glass transition temperature close to or higher than body temperature, but lower then the decomposition or degradation temperature of the therapeutic agent. However, the pre-determined erosion of the depot material can also be used to provide for slow release of the loaded therapeutic agent(s).

In various embodiments, the drug depot may be designed to release the local anesthetic such as bupivacaine when certain trigger points are reached (e.g., temperature, pH, etc.) when implanted in vivo. For example, the drug depot may comprise polymers that will release more drug as the body temperature reaches greater than, for example, 102° F., particularly if the drug possesses antipyretic properties. In various embodiments, depending on the site of administration, the drug depot may release more or less drug as a certain pH is reached. For example, the drug depot may be designed to release the drug as the bodily fluid having a certain pH contact the drug depot (e.g., CSF having a pH of about 7.35 to about 7.70, synovial fluid having a pH of about 7.29 to about 7.45; urine having a pH of about 4.6 to about 8.0, pleural fluids having a pH of about 7.2 to about 7.4, blood having a pH of about 7.35 to about 7.45, etc.).

In various embodiments, the depot may have a high drug loading, such that the local anesthetic such as bupivacaine and/or other therapeutic agent comprises about 5-99 wt. % of the depot, or 30-95 wt. % of the depot, 30-90 wt. % of the depot, or 50-75 wt. % of the depot, or 55-65 wt. % of the depot. In various embodiments, the amount of bupivacaine and/or other therapeutic agent are present in the depot in a range from about 40% to about 80% by weight of the depot (including 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, and any ranges between any two of these points, for instance, 40.1-50%, 50-60% and 60-70%, etc.).

In various embodiments, the drug depot may release 0.1 mg, 0.2 mg, 0.3 mg, 0.4 mg, 0.5 mg, 0.6 mg, 0.7 mg, 0.8 mg, 0.9 mg, 1 mg, 1.1 mg, 1.2 mg, 1.3 mg, 1.4 mg, 1.5 mg, 1.6 mg, 1.7 mg, 1.8 mg, 1.9 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 30 mg, 35 mg, or 40 mg, 45 mg, 50 mg, 55 mg, 60 mg, 65 mg, 70 mg, 75 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 300 mg, 400 mg, 500 mg, 600 mg, 700 mg 800 mg, 900 mg, or 1,000 mg of bupivacaine per day and all subranges therebetween for a total of at least 4 days, at least 7 days, at least 8 days, 4 to 30 days, 4 to 10 days, 4 to 8 days, 5 to 7 days, or 7 to 10 days. In various embodiments, the drug depot may release 0.5 mg to 20 mg of bupivacaine per hour for a total of at least 4 days, 4 to 10 days, 5 to 7 days or 7 to 10 days to reduce, treat or prevent an infection. In various embodiments, the drug depot releases 5%, 10%, 15%, 20%, 25%, 30%, 35%, 40%, 45%, 50%, 55%, 60%, 65%, 70%, 75%, 80%, 85%, 90%, 95%, 99%, or 100% of the bupivacaine over a period of 3 to 10 days, 4 to 10 days, or 5 to 7 days after the drug depot is administered to the target site. The drug depot may have a "release rate profile" that refers to the percentage of active ingredient that is released over fixed units of time, e.g., mg/hr, mg/day, 10% per day for ten days, etc. As persons of ordinary skill know, a release rate profile may be but need not be linear. By way of a non-limiting example, the drug depot may be a strip or a ribbon-like strip or fiber that releases the bupivacaine over a period of time.

In various embodiments, the drug depot comprises from about 40% to 80% by weight bupivacaine, 15% to 55% by weight of a polymer and 5% to 15% by weight of an excipient. mPEG may be used as an excipient or plasticizer for a polymer as it imparts malleability to the resulting formulation. PEG 300 may also be used as an excipient. In addition, a combination of PEG 300 and NMP may be used as the excipient.

Exemplary excipients that may be formulated with bupivacaine in addition to the biodegradable polymer include but are not limited to MgO (e.g., 1 wt. %), 5050 DLG 6E, 5050 DLG 1A, mPEG, TBO-Ac, mPEG, Span-65, Span-85, pluronic F127, TBO-Ac, sorbital, cyclodextrin, maltodextrin and combinations thereof. In some embodiments, the excipient or excipients may comprise from about 0.001 wt. % to about 50 wt. % of the formulation. In some embodiments, the excipient (s) comprise from about 0.001 wt. % to about 40 wt. % of the formulation. In some embodiments, the excipient(s) comprise from about 0.001 wt. % to about 30 wt. % of the formulation. In some embodiments, the excipient(s) comprise from about 0.001 wt. % to about 20 wt. % of the formulation. In some embodiments, the excipient(s) comprise from about 0.5 wt. % to about 20 wt. % of the formulation. In some embodiments, the excipient(s) comprise from about 0.001 wt. % to about 10 wt. % of the formulation. In some embodiments, the excipient(s) comprise from about 0.001 wt. % to about 2 wt. % of the formulation.

In some embodiments, the drug depot may not be biodegradable. For example, the drug depot may comprise polyurethane, polyurea, polyether(amide), PEBA, thermoplastic elastomeric olefin, copolyester, and styrenic thermoplastic elastomer, steel, aluminum, stainless steel, titanium, metal alloys with high non-ferrous metal content and a low relative proportion of iron, carbon fiber, glass fiber, plastics, ceramics or combinations thereof. Typically, these types of drug depots may need to be removed after a certain amount of time after administration.

In some instances, it may be desirable to avoid having to remove the drug depot after use. In those instances, the drug depot may comprise a biodegradable material. There are numerous materials available for this purpose and having the characteristic of being able to breakdown or disintegrate over a prolonged period of time when positioned at a target site. As a function of the chemistry of the biodegradable material, the mechanism of the degradation process can be hydrolytical or enzymatical in nature, or both. In various embodiments, the degradation can occur either at the surface (heterogeneous or surface erosion) or uniformly throughout the drug delivery system depot (homogeneous or bulk erosion).

The drug depot may comprise a polymeric or non-polymeric material as well as a synthetic or naturally occurring material, or a combination thereof. Non-polymeric materials include, for example, cholesterol, stigmasterol, glycerol, estradiol, sucrose, distearate, sorbitan, sorbitan monooleate, sorbitan monopalmitate, sorbitan tristearate, or the like.

In various embodiments, the drug depot comprises a polymer and the polymer can degrade in vivo over a period of less than a year, with at least 50% of the polymer degrading within six months or less. In some embodiments, the polymer is capable of or will degrade in two months, one month or less. In some embodiments, the polymer will degrade significantly within a month, with at least 50% of the polymer degrading into non-toxic residues which are removed by the body, and 100% of the drug being released within a two week period. Polymers should also degrade by hydrolysis by surface erosion, rather than by bulk erosion, so that release is not only sustained but also linear. Polymers which meet this criteria include some of the polyanhydrides, co-polymers of lactic acid and glycolic acid wherein the weight ratio of lactic acid to glycolic acid is no more than 4:1 (i.e., 80% or less lactic acid to 20% or more glycolic acid by weight), and polyorthoesters containing a catalyst or degradation enhancing compound, for example, containing at least 1% by weight anhydride catalyst such as maleic anhydride. Other polymers include protein polymers such as gelatin and fibrin and polysaccharides such as hyaluronic acid.

A "depot" includes but is not limited to capsules, microspheres, microparticles, microcapsules, microfibers, particles, nanospheres, nanoparticles, coatings, matrices, wafers, pills, pellets, emulsions, liposomes, micelles, sheets, strips, ribbon-like strips or fibers, mesh, a paste, a slab, pellets, gels, or other pharmaceutical delivery compositions. Suitable materials for the depot are ideally pharmaceutically acceptable biodegradable and/or any bioabsorbable materials that are preferably FDA approved or GRAS materials. These materials can be polymeric or non-polymeric, as well as synthetic or naturally occurring, or a combination thereof.

The term "biodegradable" includes that all or parts of the drug depot will degrade over time by the action of enzymes, by hydrolytic action and/or by other similar mechanisms in the human body. In various embodiments, "biodegradable" includes that the depot (e.g., microparticle, microsphere, gel, etc.) can break down or degrade on or within the body to non-toxic components after or while a therapeutic agent has been or is being released. By "bioerodible," it is meant that the depot and/or gel will erode or degrade over time due, at least in part, to contact with substances found in the surrounding tissue, fluids or by cellular action. By "bioabsorbable," it is meant that the depot will be broken down and absorbed on or within the human body, for example, by a cell or tissue. "Biocompatible" means that the depot will not cause substantial tissue irritation or necrosis at the target site.

In various embodiments, the depot may comprise a bioabsorbable, a bioerodible, and/or a biodegradable biopolymer that may provide immediate release, sustained release or controlled release of the drug. Examples of suitable sustained release biopolymers include but are not limited to poly(alpha-hydroxy acids), poly(lactide-co-glycolide) (PLGA or DLG) (which includes poly(lactide-co-glycolide), poly(D-lactide-co-glycolide), poly(L-lactide-co-glycolide) and poly(D,L-lactide-co-glycolide), polylactide (PLA), polyglycolide (PG), polyorthoester(s) (POE), polyethylene glycol (PEG), PEG 200, PEG 300, PEG 400, PEG 500, PEG 550, PEG 600, PEG 700, PEG 800, PEG 900, PEG 1000, PEG 1450, PEG 3350, PEG 4500, PEG 8000, conjugates of poly(alpha-hydroxy acids), polyaspirins, polyphosphagenes, collagen, starch, pre-gelatinized starch, hyaluronic acid, chitosans, gelatin, alginates, albumin, fibrin, vitamin E analogs, such as alpha tocopheryl acetate, d-alpha tocopheryl succinate, D-lactide, D,L-lactide, L-lactide, D,L-lactide-caprolactone (DL-CL), D,L-lactide-glycolide-caprolactone (DL-G-CL), dextrans, vinylpyrrolidone, polyvinyl alcohol (PVA), PVA-g-PLGA, PEGT-PBT copolymer (polyactive), methacrylates, poly(N-isopropylacrylamide), PEO-PPO-PEO (pluronics), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate) hydroxypropyl cellulose, hydroxypropyl methylcellulose, hydroxyethyl methylcellulose, carboxymethylcellulose or salts thereof, Carbopol, poly(hydroxyethylmethacrylate), poly(methoxyethylmethacrylate), poly(methoxyethoxy-ethylmethacrylate), polymethylmethacrylate (PMMA), methylmethacrylate (MMA), gelatin, polyvinyl alcohols, propylene glycol, or combinations thereof.

In various embodiments, the molecular weight of the polymer can be a wide range of values. The average molecular weight of the polymer can be from about 1000 to about 10,000,000; or about 1,000 to about 1,000,000; or about 5,000 to about 500,000; or about 10,000 to about 100,000; or about 20,000 to 50,000.

In some embodiments, the polymer comprises PLGA or POE or a combination thereof. The PLGA may comprise a mixture of polyglycolide and polylactide and in some embodiments, in the mixture, there is more polylactide than polyglycolide. In various embodiments, there is 100% polylactide and 0% polyglycolide; 95% polylactide and 5% polyglycolide; 90% polylactide and 10% polyglycolide; 85% polylactide and 15% polyglycolide; 80% polylactide and 20% polyglycolide; 75% polylactide and 25% polyglycolide; 70% polylactide and 30% polyglycolide; 65% polylactide and 35% polyglycolide; 60% polylactide and 40% polyglycolide; 55% polylactide and 45% polyglycolide; 50% polylactide and 50% polyglycolide; 45% polylactide and 55% polyglycolide; 40% polylactide and 60% polyglycolide; 35% polylactide and 65% polyglycolide; 30% polylactide and 70% polyglycolide; 25% polylactide and 75% polyglycolide; 20% polylactide and 80% polyglycolide; 15% polylactide and 85% polyglycolide; 10% polylactide and 90% polyglycolide; 5% polylactide and 95% polyglycolide; and 0% polylactide and 100% polyglycolide.

In various embodiments that comprise both polylactide and polyglycolide; there is at least 95% polylactide; at least 90% polylactide; at least 85% polylactide; at least 80% polylactide; at least 75% polylactide; at least 70% polylactide; at least 65% polylactide; at least 60% polylactide; at least 55%; at least 50% polylactide; at least 45% polylactide; at least 40% polylactide; at least 35% polylactide; at least 30% polylactide; at least 25% polylactide; at least 20% polylactide; at least 15% polylactide; at least 10% polylactide; or at least 5% polylactide; and the remainder of the biopolymer is polyglycolide.

In various embodiments, when the drug depot comprises a polymer, it is employed at about 10 wt. % to about 90 wt. %, about 10 wt. % to about 80 wt. %, about 10 wt. % to about 70 wt. %, about 15 wt. % to about 55 wt. %, about 10 wt. % to about 50 wt. %, about 25 wt. % to about 45 wt. %, about 30 wt. % to about 35 wt. % or about 20 wt. % to about 40 wt. % based on the weight of the drug depot.

In some embodiments, at least 75% of the particles have a size from about 1 micrometer to about 200 micrometers. In some embodiments, at least 85% of the particles have a size from about 1 micrometer to about 200 micrometers. In some embodiments, at least 95% of the particles have a size from about 1 micrometer to about 200 micrometers. In some embodiments, all of the particles have a size from about 1 micrometer to about 200 micrometers.

In some embodiments, at least 75% of the particles have a size from about 20 micrometers to about 100 micrometers. In some embodiments, at least 85% of the particles have a size from about 20 micrometers to about 100 micrometers. In some embodiments, at least 95% of the particles have a size from about 20 micrometers to about 100 micrometers. In some embodiments, all of the particles have a size from about 20 micrometers to about 100 micrometers.

In some embodiments, the polymer comprises DL-CL or a combination thereof. The DL-CL may comprise a mixture of lactide and caprolactone. The molar ratio of lactide to caprolactone can be 10:90 to 90:10 and all subranges therebetween (e.g., 20:80, 30:70, 45:55, 65:35, 67:33, 89:11, etc.).

In some embodiments, the polymer comprises DL-G-CL or a combination thereof. The DL-G-CL may comprise a mixture of lactide, glycolide and caprolactone. In some embodiments, the molar ratio of lactide to glycolide to caprolactone may be 30:20:50. In some embodiments, the mixture may comprise 5-50% lactide, 5-50% glycolide, and 20-80% caprolactone.

The depot may optionally contain inactive materials such as buffering agents and pH adjusting agents such as potassium bicarbonate, potassium carbonate, potassium hydroxide, sodium acetate, sodium borate, sodium bicarbonate, sodium carbonate, sodium hydroxide or sodium phosphate; degradation/release modifiers; drug release adjusting agents; emulsifiers; preservatives such as benzalkonium chloride, chlorobutanol, phenylmercuric acetate and phenylmercuric nitrate, sodium bisulfite, sodium bisulfate, sodium thiosulfate, thimerosal, methyl and other paraben, polyvinyl alcohol and phenylethyl alcohol; solubility adjusting agents; stabilizers; and/or cohesion modifiers. Typically, any such inactive materials will be present within the range of 0-75 wt. %, and more typically within the range of 0-30 wt. %. If the depot is to be placed in the spinal area or joint area, in various embodiments, the depot may comprise sterile preservative free material.

The depot can be of different sizes, shapes and configurations. There are several factors that can be taken into consideration in determining the size, shape and configuration of the drug depot. For example, both the size and shape may allow for ease in positioning the drug depot at the target site that is selected as the administration, implantation or injection site. In addition, the shape and size of the system should be selected so as to minimize or prevent the drug depot from moving after administration, implantation or injection. In various embodiments, the drug depot can be shaped like a sphere, a cylinder such as a rod or fiber, a flat surface such as a disc, film, ribbon, strip or sheet, a paste, a slab, microparticles, nanoparticles, pellets, mesh or the like. Flexibility may be a consideration so as to facilitate placement of the drug depot. In various embodiments, the drug depot can be different sizes, for example, the drug depot may be a length of from about 0.5 mm to 100 mm and have a diameter or thickness of from about 0.01 to about 5 mm. In various embodiments, the drug depot may have a layer thickness of from about 0.005 to 5.0 mm, such as, for example, from 0.05 to 2.0 mm. In some embodiments, the shape may be a strip or a ribbon-like strip and the strip or ribbon-like strip has a ratio of width to thickness in the range of 2 to 20 or greater.

Radiographic markers can be included on or in the drug depot to permit the user to accurately position the depot into the target site of the patient. These radiographic markers will also permit the user to track movement and degradation of the depot at the site over time. In this embodiment, the user may accurately position the depot in the site using any of the numerous diagnostic imaging procedures. Such diagnostic imaging procedures include, for example, X-ray imaging or fluoroscopy. Examples of such radiographic markers include, but are not limited to, barium, calcium, and/or metal beads or particles. Where present, the radiographic marker is typically present in an amount of from about 10% to about 40% (including 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39% and 40%, as well as ranges between any two of these values, e.g., 10-15%, 15-20%, 20-25%, 25-30%, 30-35%, 35-40%, and so forth, with 15-30% being more typical, even more typically 20-25%). In various embodiments, the radiographic marker could be a spherical shape or a ring around the depot.

In some embodiments, the drug depot has pores that allow release of the drug from the depot. The drug depot will allow fluid in the depot to displace the drug. However, cell infiltration into the depot will be prevented by the size of the pores of the depot. In this way, in some embodiments, the depot will not function as a tissue scaffold and will not allow tissue growth. Rather, the drug depot will be utilized for drug delivery. Thus, the drug depot will have pore sizes less than 250 microns or 500 microns so as to prevent influx of cells so that the drug depot does not function as a tissue scaffold. In other embodiments, the depot has no pores and degrades based on the action of enzymes, by hydrolytic action and/or by other similar mechanisms in the human body. In other embodiments, the drug depot may have pore sizes above 500 microns to allow influx of cells and drug release and the drug depot may function, in this embodiment, as a tissue scaffold.

In one embodiment, a drug depot for delivering a therapeutic agent to a target tissue site beneath the skin of a patient is provided, the drug depot comprising an effective amount of bupivacaine, wherein the target tissue site comprises at least one muscle, ligament, tendon, cartilage, spinal disc, spinal foraminal space near the spinal nerve root, facet or synovial joint, or spinal canal. The target tissue site may comprise an infection or the depot may be implanted at the site to prevent an infection.

In various embodiments, the drug depot comprises a gel, which includes a substance having gelatinous, jelly-like, or colloidal properties at room temperature. The gel, in various embodiments, may have the bupivacaine and optionally one or more additional therapeutic agents dispersed throughout it or suspended within the gel. The dispersal of the therapeutic agent may be even throughout the gel. Alternatively, the concentration of the therapeutic agent may vary throughout it. As the biodegradable material of the gel or drug depot degrades at the site, the therapeutic agent is released.

When the drug depot is a gel, in contrast to a sprayable gel that typically employs a low viscosity polymer, a gel with a higher viscosity may be desirable for other applications, for example, a gel having a putty-like consistency may be more preferable for bone regeneration applications. In various embodiments, when a polymer is employed in the gel, the polymeric composition includes about 10 wt. % to about 50 wt. % or about 15 wt. % to about 30 wt. % of the polymer.

In another embodiment, the gel is in viscous form and is loaded with one or more drug depots (e.g., microspheres loaded with a therapeutic agent), wherein the viscous gel is positioned into an infected site such as a wound site, synovial joint, disc space, a spinal canal, or a soft tissue surrounding the spinal canal of a subject. The gel can also be used, in various embodiments, to seal or repair tissue. In yet another embodiment, the gel is injectable, and/or an adherent gel that solidifies upon contact with tissue. For example, the gel may be administered as a liquid that gels in situ at the target tissue site. In various embodiments, the gel can comprise a two part system where a liquid is administered and a gelling agent is added subsequently to cause the liquid to gel or harden.

In various embodiments, the gel is a hardening gel, where after the gel is applied to the target site, it hardens and the drug can be released as the bodily fluid contacts the gel.

In various embodiments, the drug depot is loaded with bupivacaine and optionally one or more additional therapeutic agents, and delivered to a desired target tissue site (e.g., infected surgical wound site, infected tissue site, etc.) and, in various embodiments, the drug depot may be held in place by a suture, barb, staple, adhesive gel, etc. which prevents the drug depot from being removed from that site by the venous systemic circulation or otherwise dispersed too widely, which reduces the desired therapeutic effect. For example, after hours or days, the drug depot may degrade, thereby allowing the drug depots (e.g., strips, ribbon-like strips, etc.) to begin releasing the therapeutic agent. The strips may be formed from an insoluble or inert substance, but soluble or active once it comes into contact with the target tissue site. Likewise, the drug depot may comprise a substance that dissolves or disperses within the tissue. As the drug depot begins to dissolve within hours to days, the drug depots (e.g., strips) are exposed to body fluids and begin releasing their contents. The drug depot can be formulated to optimize exposure time of the drug depot and release of the therapeutic agent from the drug depot.

In various embodiments, the drug depot (e.g., gel) is flowable and can be injected, sprayed, instilled, and/or dispensed to, on or in the target site. "Flowable" means that the gel formulation is easy to manipulate and may be brushed, sprayed, dripped, painted, injected, shaped and/or molded at or near the target site as it coagulates. "Flowable" includes formulations with a low viscosity or water-like consistency to those with a high viscosity, such as a paste-like material. In various embodiments, the flowability of the formulation allows it to conform to irregularities, crevices, cracks, and/or voids in the site. For example, in various embodiments, the gel may be used to fill one or more voids in an osteolytic lesion.

In various embodiments, the drug depot comprises poly (alpha-hydroxy acids), PLGA, D,L-lactide-glycolide-ϵ-caprolactone, PLA, PG, polyethylene glycol conjugates of poly (alpha-hydroxy acids), polyorthoesters, polyaspirins, polyphosphagenes, collagen, starch, pre-gelatinized starch, hyaluronic acid, chitosans, gelatin, alginates, albumin, fibrin, vitamin E analogs, such as alpha tocopheryl acetate, d-alpha tocopheryl succinate, D,L-lactide, D-lactide, L-lactide, D,L-lactide-caprolactone, D,L-lactide-glycolide-caprolactone, dextrans, vinylpyrrolidone, polyvinyl alcohol (PVA), PVA-g-PLGA, PEGT-PBT copolymer (polyactive), methacrylates, poly(N-isopropylacrylamide), PEO-PPO-PEO (pluronics), PEO-PPO-PAA copolymers, PLGA-PEO-PLGA, PEG-PLG (poly(d,l-lactide-co-glycolide), PLA-PLGA, poloxamer 407, PEG-PLGA-PEG triblock copolymers, SAIB (sucrose acetate isobutyrate) or combinations thereof. These one or more components allow the therapeutic agent to be released from the drug depot in a controlled and/or sustained manner. For example, the drug depot containing the therapeutic agent and a polymer matrix can be injected at the target site and the polymer matrix breaks down over time (e.g., hours, days) on or within the target site releasing bupivacaine and optionally additional therapeutic agents. Thus, the administration of the drug depot can be localized and occur over a period of time (e.g., at least one day to about 2, 3, 4, 5, 6, 7, 8, 9, 10, 11, 12, 13, 14, 15, 16, 17, 18, 19, 20, 21, 22, 23, 24, 25, 26, 27, 28, 29 and 30 days).

The terms "sustained release" or "sustain release" (also referred to as extended release or controlled release) are used herein to refer to one or more therapeutic agent(s) that is introduced on or into the body of a human or other mammal and continuously releases a stream of one or more therapeutic agents over a predetermined time period and at a therapeutic level sufficient to achieve a desired therapeutic effect throughout the predetermined time period. Reference to a continuous release stream is intended to encompass release that occurs as the result of biodegradation in vivo of drug depot, or a matrix or component thereof, or as the result of metabolic transformation or dissolution of the therapeutic agent(s) or conjugates of therapeutic agent(s).

The phrase "immediate release" is used herein to refer to one or more therapeutic agent(s) that is introduced into the body and that is allowed to dissolve in or become absorbed at the location to which it is administered, with no intention of delaying or prolonging the dissolution or absorption of the drug.

The two types of formulations (sustain release and immediate release) may be used in conjunction. The sustained release and immediate release may be in one or more of the same depots. In various embodiments, the sustained release and immediate release may be part of separate depots. For example, a bolus or immediate release formulation of bupivacaine may be placed at or near the target site and a sustain release formulation may also be placed at or near the same site. Thus, even after the bolus becomes completely accessible, the sustain release formulation would continue to provide the active ingredient for the intended site.

In various embodiments, the drug depot is designed to cause an initial burst dose of therapeutic agent within the first 48 hours or 24 hours after administration. "Initial burst" or "burst effect" or "bolus dose" refers to the release of therapeutic agent from the drug depot during the first 48 hours or 24 hours after the drug depot comes in contact with an aqueous fluid (e.g., fluid at a wound site, synovial fluid, cerebral spinal fluid, etc.). In some embodiments, the drug depot is designed to avoid this initial burst effect.

In various embodiments, the drug depot contains one or more different release layer(s) that releases a bolus dose of bupivacaine or pharmaceutically acceptable salt thereof (e.g., 100 mg to 800 mg, 400-800 mg, or 100 mg to 200 mg at a target site) and one or more sustain release layer(s) that releases an effective amount of bupivacaine or pharmaceutically acceptable salt thereof over a period of 3 to 30 days, 3 to 10 days, or 7 to 10 days. In various embodiments, the one or more immediate release layer(s) comprise PLGA, which degrades faster than the one or more sustain release layer(s), which comprises PLA, which degrades at a slower rate than the PLGA.

In various embodiments, when the drug depot comprises a gel, the gel may have a pre-dosed viscosity in the range of about 1 to about 500 centipoise (cps), 1 to about 200 cps, or 1 to about 100 cps. After the gel is administered to the target site, the viscosity of the gel will increase.

In one embodiment, the gel may be an adherent gel, which comprises a therapeutic agent that is evenly distributed throughout the gel. The gel may be of any suitable type, as previously indicated, and should be sufficiently viscous so as to prevent the gel from migrating from the targeted delivery site once deployed; the gel should, in effect, "stick" or adhere to the targeted site. The gel may, for example, solidify upon contact with the targeted site or after deployment from a targeted delivery system. The targeted delivery system may be, for example, a syringe, a catheter, needle or cannula or any other suitable device. The targeted delivery system may inject or spray the gel into or on the targeted site. The therapeutic agent may be mixed into the gel prior to the gel being deployed at the targeted site. In various embodiments, the gel may be part of a two-component delivery system and when the two components are mixed, a chemical process is activated to form the gel and cause it to stick or adhere to the target site.

In various embodiments, for those gel formulations that contain a polymer, the polymer concentration may affect the rate at which the gel hardens (e.g., a gel with a higher concentration of polymer may coagulate more quickly than gels having a lower concentration of polymer). In various embodiments, when the gel hardens, the resulting matrix is solid but is also able to conform to the irregular surface of a target site such as a tissue (e.g., recesses and/or projections in bone).

The percentage of polymer present in the gel may also affect the viscosity of the polymeric composition. For example, a composition having a higher percentage by weight of polymer is typically thicker and more viscous than a composition having a lower percentage by weight of polymer. A more viscous composition tends to flow more slowly. Therefore, a composition having a lower viscosity may be used in some instances, for example, when applying the formulation via spray.

In various embodiments, the molecular weight of the gel can be varied by many methods known in the art. The choice of method to vary molecular weight is typically determined by the composition of the gel (e.g., polymer, versus non-polymer). For example, in various embodiments, when the gel comprises one or more polymers, the degree of polymerization can be controlled by varying the amount of polymer initiators (e.g. benzoyl peroxide), organic solvents or activator (e.g. DMPT), crosslinking agents, polymerization agent, and/or reaction time.

Suitable gel polymers may be soluble in an organic solvent. The solubility of a polymer in a solvent varies depending on the crystallinity, hydrophobicity, hydrogen-bonding and molecular weight of the polymer. Lower molecular weight polymers will normally dissolve more readily in an organic solvent than high-molecular weight polymers. A polymeric gel, which includes a high molecular weight polymer, tends to coagulate or solidify more quickly than a polymeric composition, which includes a low-molecular weight polymer. Polymeric gel formulations, which include high molecular weight polymers, also tend to have a higher solution viscosity than a polymeric gel, which include a low-molecular weight polymer.

In various embodiments, the gel has an inherent viscosity (abbreviated as "I.V." and units are in deciliters/gram), which is a measure of the gel's molecular weight and degradation time (e.g., a gel with a high inherent viscosity has a higher molecular weight and longer degradation time). Typically, a gel with a high molecular weight provides a stronger matrix and the matrix takes more time to degrade. In contrast, a gel with a low molecular weight degrades more quickly and provides a softer matrix. In various embodiments, the gel has a molecular weight, as shown by the inherent viscosity, from about 0.10 dL/g to about 1.2 dL/g or from about 0.10 dL/g to about 0.40 dL/g. Other IV ranges include but are not limited to about 0.05 to about 0.15 dL/g, about 0.10 to about 0.20 dL/g, about 0.15 to about 0.25 dL/g, about 0.20 to about 0.30 dL/g, about 0.25 to about 0.35 dL/g, about 0.30 to about 0.35 dL/g, about 0.35 to about 0.45 dL/g, about 0.40 to about 0.45 dL/g, about 0.45 to about 0.50 dL/g, about 0.50 to about 0.70 dL/g, about 0.60 to about 0.80 dL/g, about 0.70 to about 0.90 dL/g, and about 0.80 to about 1.00 dL/g.

In various embodiments, the gel can have a viscosity of about 300 to about 5,000 centipoise (cp). In other embodiments, the gel can have a viscosity of from about 5 to about 300 cps, from about 10 cps to about 50 cps, from about 15 cps to about 75 cps at room temperature, which allows it to be sprayed at or near the target site.

In various embodiments, the drug depot may comprise material to enhance viscosity and control the release of the drug. Such material may include, for example, hydroxypropyl cellulose, hydroxypropyl methylcellulose, hydroxyethyl methylcellulose, carboxymethylcellulose and salts thereof, Carbopol, poly(hydroxyethylmethacrylate), poly(methoxyethylmethacrylate), poly(methoxyethoxy-ethylmethacrylate), polymethyl-methacrylate (PMMA), methylmethacrylate (MMA), gelatin, polyvinyl alcohols, propylene glycol, PEG 200, PEG 300, PEG 400, PEG 500, PEG 550, PEG 600, PEG 700, PEG 800, PEG 900, PEG 1000, PEG 1450, PEG 3350, PEG 4500, PEG 8000 or combinations thereof. For example, in various embodiments, the drug depot comprises from about 25% to 75% by weight bupivacaine, about 15% to 75% by weight D,L-lactide-glycolide-caprolactone, and about 5% to 10% by weight of PEG 300. The drug depot can also comprise from about 1% to 15% NMP.

The drug depot release profile can also be controlled, among other things, by controlling the particle size distribution of the components of the drug depot. In various embodiments, the particle size distribution of the components of the drug depot (e.g., bupivacaine, gel, etc.) may be in the range of from about 10 µM to 200 µM so that the drug depot can easily be delivered to or at or near the target site by injection, spraying, instilling, etc. In various embodiments, the particle size may be 10 µM, 13 µM, 85 µM, 100 µM, 151 µM, 200 µM and all subranges therebetween.

In various embodiments, the drug depot may comprise a hydrogel made of high molecular weight biocompatible elastomeric polymers of synthetic or natural origin. A desirable property for the hydrogel to have is the ability to respond rapidly to mechanical stresses, particularly shears and loads, in the human body.

Hydrogels obtained from natural sources are particularly appealing since they are more likely to be biodegradable and biocompatible for in vivo applications. Suitable hydrogels include natural hydrogels, such as for example, gelatin, collagen, silk, elastin, fibrin and polysaccharide-derived polymers like agarose, and chitosan, glucomannan gel, hyaluronic acid, polysaccharides, such as cross-linked carboxyl-containing polysaccharides, or a combination thereof. Synthetic hydrogels include, but are not limited to those formed from polyvinyl alcohol, acrylamides such as polyacrylic acid and poly(acrylonitrile-acrylic acid), polyurethanes, polyethylene glycol (e.g., PEG 3350, PEG 4500, PEG 8000), silicone, polyolefins such as polyisobutylene and polyisoprene, copolymers of silicone and polyurethane, neoprene, nitrile, vulcanized rubber, poly(N-vinyl-2-pyrrolidone), acrylates such as poly(2-hydroxy ethyl methacrylate) and copolymers of acrylates with N-vinyl pyrolidone, N-vinyl lactams, polyacrylonitrile or combinations thereof. The hydrogel materials may further be cross-linked to provide further strength as needed. Examples of different types of polyurethanes include thermoplastic or thermoset polyurethanes, aliphatic or aromatic polyurethanes, polyetherurethane, polycarbonate-urethane or silicone polyether-urethane, or a combination thereof.

In various embodiments, rather than directly admixing the therapeutic agent into the gel, microspheres may be dispersed within the gel, the microspheres being loaded with bupivacaine. In one embodiment, the microspheres provide for a sustained release of the bupivacaine. In yet another embodiment, the gel, which is biodegradable, prevents the microspheres from releasing the bupivacaine; the microspheres thus do not release the bupivacaine until they have been released from the gel. For example, a gel may be deployed around an infected target tissue site (e.g., a nerve root). Dispersed within the gel are a plurality of microspheres that encapsulate the desired therapeutic agent. Certain of these microspheres degrade once released from the gel, thus releasing the bupivacaine.

Microspheres, much like a fluid, may disperse relatively quickly, depending upon the surrounding target site, and hence disperse the bupivacaine. In some situations, this may be desirable; in others, it may be more desirable to keep the bupivacaine tightly constrained to a well-defined target site. The present invention also contemplates the use of adherent gels to so constrain dispersal of the therapeutic agent.

Drug Delivery

It will be appreciated by those with skill in the art that the depot can be administered to the target site using a "cannula" or "needle" that can be a part of a drug delivery device e.g., a syringe, a gun drug delivery device, or any medical device suitable for the application of a drug to the target site. The cannula or needle of the drug depot device is designed to cause minimal physical and psychological trauma to the patient.

Cannulas or needles include tubes that may be made from materials, such as for example, polyurethane, polyurea, polyether(amide), PEBA, thermoplastic elastomeric olefin, copolyester, and styrenic thermoplastic elastomer, steel, aluminum, stainless steel, titanium, metal alloys with high non-ferrous metal content and a low relative proportion of iron, carbon fiber, glass fiber, plastics, ceramics or combinations thereof. The cannula or needle may optionally include one or more tapered regions. In various embodiments, the cannula or needle may be beveled. The cannula or needle may also have a tip style vital for accurate treatment of the patient depending on the site for implantation. Examples of tip styles include, for example, Trephine, Cournand, Veress, Huber, Seldinger, Chiba, Francine, Bias, Crawford, deflected tips, Hustead, Lancet, or Tuohey. In various embodiments, the cannula or needle may also be non-coring and have a sheath covering it to avoid unwanted needle sticks.

The dimensions of the hollow cannula or needle, among other things, will depend on the site of administration. Some examples of lengths of the cannula or needle may include, but are not limited to, from about 50 to 150 mm in length, for example, about 65 mm for epidural pediatric use, about 85 mm for a standard adult and about 110 mm for an obese adult patient. The thickness of the cannula or needle will also depend on the site of administration or target site. In various embodiments, the thickness includes, but is not limited to, from about 0.05 to about 1.655. The gauge of the cannula or needle may be the widest or smallest diameter or a diameter in between for insertion into a human or animal body. The widest diameter is typically about 14 gauge, while the smallest diameter is about 22 gauge. In various embodiments the gauge of the needle or cannula is about 18 to about 22 gauge.

In various embodiments, like the drug depot and/or gel, the cannula or needle includes dose radiographic markers that indicate location at or near the target site, so that the user may accurately position the depot at or near the site using any of the numerous diagnostic imaging procedures. Such diagnostic imaging procedures include, for example, X-ray imaging or fluoroscopy. Examples of such radiographic markers include, but are not limited to, barium, calcium, and/or metal beads or particles.

In various embodiments, the needle or cannula may include a transparent or translucent portion that can be visualizable by ultrasound, fluoroscopy, x-ray, or other imaging techniques. In such embodiments, the transparent or translucent portion may include a radiopaque material or ultrasound responsive topography that increases the contrast of the needle or cannula relative to the absence of the material or topography.

The drug depot, and/or medical device to administer the drug may be sterilizable. In various embodiments, one or more components of the drug depot, and/or medical device to administer the drug are sterilized by radiation in a terminal sterilization step in the final packaging. Terminal sterilization of a product provides greater assurance of sterility than from processes such as an aseptic process, which require individual product components to be sterilized separately and the final package assembled in a sterile environment.

Typically, in various embodiments, gamma radiation is used in the terminal sterilization step, which involves utilizing ionizing energy from gamma rays that penetrates deeply in the device. Gamma rays are highly effective in killing microorganisms, they leave no residues nor have sufficient energy to impart radioactivity to the device. Gamma rays can be employed when the device is in the package and gamma sterilization does not require high pressures or vacuum conditions, thus, package seals and other components are not stressed. In addition, gamma radiation eliminates the need for permeable packaging materials.

In various embodiments, electron beam (e-beam) radiation may be used to sterilize one or more components of the device. E-beam radiation comprises a form of ionizing energy, which is generally characterized by low penetration and high-dose rates. E-beam irradiation is similar to gamma processing in that it alters various chemical and molecular bonds on contact, including the reproducing cells of microorganisms. Beams produced for e-beam sterilization are concentrated, highly-charged streams of electrons generated by the acceleration and conversion of electricity. E-beam sterilization may be used, for example, when the drug depot is included in a gel.

Other methods may also be used to sterilize the depot and/or one or more components of the device, including, but not limited to, gas sterilization, such as, for example, with ethylene oxide or steam sterilization.

In various embodiments, a kit is provided that may include additional parts along with the drug depot and/or medical device combined together to be used to administer the drug depot (e.g., ribbon-like strips). The kit may include the drug depot device in a first compartment. The second compartment may include a canister holding the drug depot and any other instruments needed for the drug delivery. A third compartment may include gloves, drapes, wound dressings and other procedural supplies for maintaining sterility of the administration process, as well as an instruction booklet. A fourth compartment may include additional cannulas and/or needles. Each tool may be separately packaged in a plastic pouch that is radiation sterilized. A cover of the kit may include illustrations of the administration procedure and a clear plastic cover may be placed over the compartments to maintain sterility.

In various embodiments, a method for delivering bupivacaine into a target site of a patient is provided. The target site is an infected site or a potentially infected site. The method comprises inserting a cannula or needle at or near a target site and administering the drug depot containing the bupivacaine at the target site of the patient. In various embodiments, to administer the drug depot to the desired site, first the cannula or needle can be inserted through the skin and soft tissue down to the target site and the drug depot administered (e.g., injected, implanted, instilled, sprayed, etc.) at or near the target site. In those embodiments where the drug depot is separate from the gel, first the cannula or needle can be inserted through the skin and soft tissue down to the site of injection and one or more base layer(s) of gel can be administered to the target site. Following administration of the one or more base layer(s), the drug depot can be administered on or in the base layer(s) so that the gel can hold the depot in place or reduce migration. If required, a subsequent layer or layers of gel can be applied on the drug depot to surround the depot and further hold it in place. Alternatively, the drug depot may be implanted or injected first and then the gel placed (e.g., brushed, dripped, injected, or painted, etc.) around the drug depot to hold it in place. By using the gel, accurate and precise administration of a drug depot can be accomplished with minimal physical and psychological trauma to the patient. In various embodiments, the drug depot can be sutured to the target site or alternatively the drug depot can be administered, without suturing. For example, in various embodiments, the drug depot can be a strip-shaped or ribbon-shaped depot and placed at the target site, before, during or after surgery. As another example, the drug depot can be delivered in the form of a gel via a syringe or other injectable delivery directly to the target site, before, during or after surgery.

In various embodiments, when the target site comprises a spinal region, a portion of fluid (e.g., spinal fluid, etc.) can be withdrawn from the target site through a cannula or needle first and then the depot administered (e.g., placed, dripped, injected, or implanted, etc.). The target site will re-hydrate (e.g., replenishment of fluid) and this aqueous environment will cause the drug to be released from the depot.

Treating or treatment of an infection or condition refers to executing a protocol, which may include administering one or more drugs to a patient (human, other normal or otherwise), in an effort to alleviate signs or symptoms of the infection. Alleviation can occur prior to signs or symptoms of the infection or condition appearing, as well as after their appearance. Thus, "treating" or "treatment" may include "preventing" or "prevention" of an infection or an undesirable condition. In addition, "treating" or "treatment" does not require complete alleviation of signs or symptoms, does not require a cure, and specifically includes protocols that have only a marginal effect on the patient. "Reducing" includes a decrease in the condition and does not require complete alleviation of the signs or symptoms, and does not require a cure. In various embodiments, reducing an infection includes even a marginal decrease in the infection. By way of example, the administration of one or more effective dosages of bupivacaine may be used to prevent, treat or relieve an infection incidental to surgery.

"Localized" delivery includes delivery where one or more drugs are deposited within, at or near a tissue. For example, localized delivery includes delivery to a nerve root of the nervous system or a region of the brain, or in close proximity (within about 10 cm, or preferably within about 5 cm, for example) thereto. "Targeted delivery system" provides delivery of one or more drugs depots (e.g., gels or depot dispersed in the gel, etc.) having a quantity of therapeutic agent that can be deposited at or near a target tissue site as needed for treatment of an infection incidental to surgery.

FIG. 1 illustrates a number of common locations within a patient that may be sites at which surgery took place. It will be recognized that the locations illustrated in FIG. 1 are merely exemplary of the many different locations within a patient that may be at which surgery took place. For example, surgery may be required at a patient's knees 21, hips 22, fingers 23, thumbs 24, neck 25, and spine 26. Thus, during or following these surgeries, the patient may be experiencing an infection at any of these sites.

The target site includes any site which is a site of infection or potential infection. For example, the target site can be a wound site that is infected or has the potential to become infected. A drug depot as provided herein can be administered to the wound site to treat an existing infection or prevent an infection if no infection exists. The drug depot can be administered in many forms as provided herein. One embodiment contemplates a bandage comprising the depot which would cover the wound site. The depot can provide immediate relief to an existing infection followed by continuous treatment of the infection to reduce or eliminate the infection. If no infection exists in the wound site, the depot can immediately work to reduce the likelihood of infection or prevent an infection from occurring at the wound site.

The target site can be any site such as a muscle, a ligament, a tendon, cartilage, a spinal disc, the spinal foraminal space near the spinal nerve root, a facet or synovial joint, or the spinal canal. These sites may be infected during a surgical procedure (e.g., hernia repair, orthopedic or spine surgery, etc.) or may have the potential to be infected during a surgical procedure. Surgical procedures include any procedure that penetrates beneath the skin. Surgical procedures also include arthroscopic surgery, an excision of a mass, spinal fusion, thoracic, cervical, or lumbar surgery, pelvic surgery or a combination thereof. A drug depot can be administered to these surgical sites to treat an existing infection or prevent an infection if no infection exists.

Figure 2:
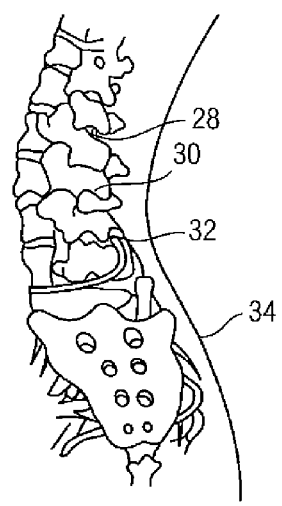
FIG. 2 illustrates a schematic dorsal view of the spine and sites where a drug depot containing an analgesic or local anesthetic can be administered thereto.

One embodiment where the depot is suitable for use in infection management is illustrated in FIG. 2. Schematically shown in FIG. 2 is a dorsal view of the spine and sites where the drug depot may be inserted using a syringe, cannula or needle beneath the skin 34 to a spinal site 32 (e.g., spinal disc space, spinal canal, soft tissue surrounding the spine, nerve root, etc.) and one or more drug depots 28 and 32 are delivered to various sites along the spine. In this way, when several drug depots are to be implanted, they are implanted in a manner that optimizes location, accurate spacing, and drug distribution.

Although the spinal site is shown, as described above, the drug depot can be delivered to any site beneath the skin, including, but not limited to, at least one muscle, ligament, tendon, cartilage, spinal disc, spinal foraminal space, near the spinal nerve root, or spinal canal. In various embodiments, the drug depot containing bupivacaine can be administered to the patient intra-operatively, intravenously, intramuscularly, continuous or intermittent infusion, intraperitoneal, intrasternal, subcutaneously, intrathecally, intradiskally, peridiskally, epidurally, perispinally, intraarticular injection, parenterally, or via combinations thereof. In some embodiments, the injection is intrathecal, which refers to an injection into the spinal canal (intrathecal space surrounding the spinal cord). An injection may also be into a muscle or other tissue.

In some embodiments, it is preferable to co-administer bupivacaine with an antagonist to counteract undesirable effects. Exemplary antagonists include but are not limited to phentolamine, yohimbine, tolazoline and piperoxane. Additionally, compounds such as 5-fluorodeoxyuridine (FUDR) and 3,4 dehydroprolene may also be included. These compounds may prevent or reduce glial and fibroblastic scar formation associated with some types of surgeries.

In some embodiments, the drug depot is suitable for parenteral administration. Parenteral administration may include, for example, an infusion pump that administers a pharmaceutical composition (e.g., anesthetic and anti-inflammatory combination) through a catheter near the spine or one or more inflamed joints, an implantable mini-pump that can be inserted at or near the target site, an implantable controlled release device or sustained release delivery system that can release a certain amount of the drug per hour or in intermittent bolus doses. One example of a suitable pump for use is the SynchroMed® (Medtronic, Minneapolis, Minn.) pump. This pump has three sealed chambers. One contains an electronic module and battery. The second contains a peristaltic pump and drug reservoir. The third contains an inert gas, which provides the pressure needed to force the pharmaceutical composition into the peristaltic pump. To fill the pump, the pharmaceutical composition is injected through the reservoir fill port to the expandable reservoir. The inert gas creates pressure on the reservoir, and the pressure forces the pharmaceutical composition through a filter and into the pump chamber. The pharmaceutical composition is then pumped out of the device from the pump chamber and into the catheter, which will direct it for deposit at the target site. The rate of delivery of pharmaceutical composition is controlled by a microprocessor. This allows the pump to be used to deliver similar or different amounts of pharmaceutical composition continuously, at specific times, or at set intervals between deliveries.

In various embodiments, where the target site comprises blood vessels, a vasoconstrictor may be employed in the drug depot. When the vasoconstrictor is released, it lengthens the duration of the anesthetic response and reduces the systemic uptake of the anesthetic agent. The anesthetic may be, for example, bupivacaine, and the vasoconstrictor may be, for example, epinephrine or phenylephrine.

The term "patient" refers to organisms from the taxonomy class "mammalian," including but not limited to humans, other primates such as chimpanzees, apes orangutans and monkeys, rats, mice, cats, dogs, cows, horses, etc.

Method of Making Depots

In various embodiments, the drug depot comprising the analgesic, local anesthetic or pharmaceutically acceptable salt thereof can be made by combining a biocompatible polymer and a therapeutically effective amount of the analgesic, local anesthetic or pharmaceutically acceptable salt thereof and forming the drug depot from the combination.

Various techniques are available for forming at least a portion of a drug depot from the biocompatible polymer(s), therapeutic agent(s), and optional materials, including solution processing techniques and/or thermoplastic processing techniques. Where solution processing techniques are used, a solvent system is typically selected that contains one or more solvent species. The solvent system is generally a good solvent for at least one component of interest, for example, a biocompatible polymer and/or a therapeutic agent. The particular solvent species that make up the solvent system can also be selected based on other characteristics, including drying rate and surface tension.

Solution processing techniques include solvent casting techniques, spin coating techniques, web coating techniques, solvent spraying techniques, dipping techniques, techniques involving coating via mechanical suspension, including air suspension (e.g., fluidized coating), ink jet techniques and electrostatic techniques. Where appropriate, techniques such as those listed above can be repeated or combined to build up the depot to obtain the desired release rate and desired thickness.

In various embodiments, a solution containing solvent and biocompatible polymer are combined and placed in a mold of the desired size and shape. In this way, polymeric regions, including barrier layers, lubricious layers, and so forth can be formed. If desired, the solution can further comprise, one or more of the following: an analgesic or local anesthetic, other therapeutic agent(s) and other optional additives such as radiographic agent(s), etc. in dissolved or dispersed form. This results in a polymeric matrix region containing these species after solvent removal. In other embodiments, a solution containing solvent with dissolved or dispersed therapeutic agent is applied to a pre-existing polymeric region, which can be formed using a variety of techniques including solution processing and thermoplastic processing techniques, whereupon the therapeutic agent is imbibed into the polymeric region.

Thermoplastic processing techniques for forming the depot or portions thereof include molding techniques (for example, injection molding, rotational molding, and so forth), extrusion techniques (for example, extrusion, co-extrusion, multi-layer extrusion, and so forth) and casting.

Thermoplastic processing in accordance with various embodiments comprises mixing or compounding, in one or more stages, the biocompatible polymer(s) and one or more of the following: an analgesic or local anesthetic, optional additional therapeutic agent(s), radiographic agent(s), and so forth. The resulting mixture is then shaped into a drug depot. The mixing and shaping operations may be performed using any of the conventional devices known in the art for such purposes.

During thermoplastic processing, there exists the potential for the therapeutic agent(s) to degrade, for example, due to elevated temperatures and/or mechanical shear that are associated with such processing. For example, if the local anesthetic is bupivacaine, it may undergo substantial degradation under ordinary thermoplastic processing conditions. Hence, processing is preferably performed under modified conditions, which prevent the substantial degradation of the therapeutic agent(s). Although it is understood that some degradation may be unavoidable during thermoplastic processing, degradation is generally limited to 10% or less. Among the processing conditions that may be controlled during processing to avoid substantial degradation of the therapeutic agent(s) are temperature, applied shear rate, applied shear stress, residence time of the mixture containing the therapeutic agent, and the technique by which the polymeric material and the therapeutic agent(s) are mixed.

Mixing or compounding the biocompatible polymer with therapeutic agent(s) and any additional additives to form a substantially homogenous mixture thereof may be performed with any device known in the art and conventionally used for mixing polymeric materials with additives.

Where thermoplastic materials are employed, a polymer melt may be formed by heating the biocompatible polymer, which can be mixed with various additives (e.g., therapeutic agent(s), inactive ingredients, etc.) to form a mixture. A common way of doing so is to apply mechanical shear to a mixture of the biocompatible polymer(s) and additive(s). Devices in which the biocompatible polymer(s) and additive(s) may be mixed in this fashion include devices such as single screw extruders, twin screw extruders, banbury mixers, high-speed mixers, ross kettles, and so forth.

Any of the biocompatible polymer(s) and various additives may be premixed prior to a final thermoplastic mixing and shaping process, if desired (e.g., to prevent substantial degradation of the therapeutic agent among other reasons).

For example, in various embodiments, a biocompatible polymer is precompounded with a radiographic agent (e.g., radio-opacifying agent) under conditions of temperature and mechanical shear that would result in substantial degradation of the therapeutic agent, if it were present. This precompounded material is then mixed with a therapeutic agent under conditions of lower temperature and mechanical shear, and the resulting mixture is shaped into the drug depot. Conversely, in another embodiment, the biocompatible polymer can be precompounded with the therapeutic agent under conditions of reduced temperature and mechanical shear. This precompounded material is then mixed with, for example, a radio-opacifying agent, also under conditions of reduced temperature and mechanical shear, and the resulting mixture is shaped into the drug depot.

The conditions used to achieve a mixture of the biocompatible polymer and therapeutic agent and other additives will depend on a number of factors including, for example, the specific biocompatible polymer(s) and additive(s) used, as well as the type of mixing device used.

As an example, different biocompatible polymers will typically soften to facilitate mixing at different temperatures. For instance, where a depot is formed comprising PLGA or PLA polymer, a radio-opacifying agent (e.g., bismuth subcarbonate), and a therapeutic agent prone to degradation by heat and/or mechanical shear, in various embodiments, the PGLA or PLA can be premixed with the radio-opacifying agent at temperatures of about, for example, 150° C. to 170°

C. The therapeutic agent is then combined with the premixed composition and subjected to further thermoplastic processing at conditions of temperature and mechanical shear that are substantially lower than is typical for PGLA or PLA compositions. For example, where extruders are used, barrel temperature, volumetric output are typically controlled to limit the shear and therefore to prevent substantial degradation of the therapeutic agent(s). For instance, the therapeutic agent and premixed composition can be mixed/compounded using a twin screw extruder at substantially lower temperatures (e.g., 100-105° C.), and using substantially reduced volumetric output (e.g., less than 30% of full capacity, which generally corresponds to a volumetric output of less than 200 cc/min). It is noted that this processing temperature is well below the melting points of local anesthetics such as bupivacaine, because processing at or above these temperatures will result in substantial therapeutic agent degradation. It is further noted that in certain embodiments, the processing temperature will be below the melting point of all bioactive compounds within the composition, including the therapeutic agent. After compounding, the resulting depot is shaped into the desired form, also under conditions of reduced temperature and shear.

In other embodiments, biodegradable polymer(s) and one or more therapeutic agents are premixed using non-thermoplastic techniques. For example, the biocompatible polymer can be dissolved in a solvent system containing one or more solvent species. Any desired agents (for example, a radio-opacifying agent, a therapeutic agent, or both radio-opacifying agent and therapeutic agent) can also be dissolved or dispersed in the solvent system. Solvent is then removed from the resulting solution/dispersion, forming a solid material. The resulting solid material can then be granulated for further thermoplastic processing (for example, extrusion) if desired.

As another example, the therapeutic agent can be dissolved or dispersed in a solvent system, which is then applied to a pre-existing drug depot (the pre-existing drug depot can be formed using a variety of techniques including solution and thermoplastic processing techniques, and it can comprise a variety of additives including a radio-opacifying agent and/or viscosity enhancing agent), whereupon the therapeutic agent is imbibed on or in the drug depot. As above, the resulting solid material can then be granulated for further processing, if desired.

Typically, an extrusion process may be used to form the drug depot comprising a biocompatible polymer(s), therapeutic agent(s) and radio-opacifying agent(s). Co-extrusion may also be employed, which is a shaping process that can be used to produce a drug depot comprising the same or different layers or regions (for example, a structure comprising one or more polymeric matrix layers or regions that have permeability to fluids to allow immediate and/or sustained drug release). Multi-region depots can also be formed by other processing and shaping techniques such as co-injection or sequential injection molding technology.

In various embodiments, the depot that may emerge from the thermoplastic processing (e.g., ribbon, pellet, strip, etc.) is cooled. Examples of cooling processes include air cooling and/or immersion in a cooling bath. In some embodiments, a water bath is used to cool the extruded depot. However, where the therapeutic agent is water-soluble, the immersion time should be held to a minimum to avoid unnecessary loss of therapeutic agent into the bath.

In various embodiments, immediate removal of water or moisture by use of ambient or warm air jets after exiting the bath will also prevent re-crystallization of the drug on the depot surface, thus controlling or minimizing a high drug dose "initial burst" or "bolus dose" upon implantation or insertion if this is release profile is not desired.

In various embodiments, the drug depot can be prepared by mixing or spraying the drug with the polymer and then molding the depot to the desired shape. In various embodiments, a local anesthetic such as bupivacaine is used and mixed or sprayed with PLGA, poly(D,L-lactide-caprolactone) polymer, and/or poly(D,L-lactide-glycolide-caprolactone) polymer and the resulting depot may be formed by extrusion and dried.

In some formulations, there may be 55-65% bupivacaine, 25-35% PLGA and 5-15% mPEG. Some of these formulations will release between 10 and 30% of the active ingredient on day 1 and all or substantially all of the active ingredient by day 10. Some of these formulations will release between 15 and 25% of the active ingredient on day 1 and all or substantially all of the product by day 10.

In still other formulations, there may be 55-65% bupivacaine, 25-35% DL-G-CL, 6% PEG 300 and 13% NMP. Some of these formulations will release between 10 and 30% of the active ingredient on day 1 and all or substantially all of the active ingredient by day 10. Some of these formulations will release between 10 and 15% of the active ingredient on day 1 and all or substantially all of the product by day 10.

In another embodiment, a drug depot useful for reducing, preventing or treating an infection in a patient in need of such treatment is provided. The drug depot comprises a therapeutically effective amount of bupivacaine or pharmaceutically acceptable salt thereof. The depot is administered at a target site to reduce, prevent or treat infections wherein the drug depot comprises (i) one or more immediate release layer(s) that is capable of releasing about 5% to about 50% of the bupivacaine or pharmaceutically acceptable salt thereof relative to a total amount of the bupivacaine or pharmaceutically acceptable salt thereof loaded in the drug depot over a first period of up to 48 hours, a first period of up to 24 hours, or a first period of about 24 to 48 hours and (ii) one or more sustain release layer(s) that is capable of releasing about 50% to about 95% of the bupivacaine or pharmaceutically acceptable salt thereof relative to a total amount of the bupivacaine or pharmaceutically acceptable salt thereof loaded in the drug depot over a subsequent period of up to 4 to 30 or 4 to 10 days. The immediate release layer allows for the release of bupivacaine immediately to treat an infection followed by sustained release of bupivacaine from the sustain release layer which provides sustained relief of the infection. The one or more immediate release layer(s) comprise one or more of poly(lactide-co-glycolide), polylactide, polyglycolide, polyorthoester, D-lactide, D,L-lactide, poly(D,L-lactide), L-lactide, poly(D,L-lactide-co-caprolactone), poly(D,L-lactide-co-glycolide-co-caprolactone), polycaprolactone or a combination thereof, and the one or more sustain release layer(s) comprise one or more of poly(lactide-co-glycolide), polylactide, polyglycolide, polyorthoester, D-lactide, D,L-lactide, poly(D,L-lactide), L-lactide, poly(D,L-lactide-co-caprolactone), poly(D,L-lactide-co-glycolide-co-caprolactone), polycaprolactone or a combination thereof.

In still another embodiment, a method of reducing an infection in a patient in need of such treatment is provided. The method comprises delivering one or more biodegradable drug depots comprising a therapeutically effective amount of bupivacaine or pharmaceutically acceptable salt thereof to a target tissue site beneath the skin before, during or after surgery, wherein the drug depot is capable of releasing an initial bolus dose of an effective amount of bupivacaine or pharmaceutically acceptable salt thereof at the site beneath the skin followed by a sustained release dose of an effective amount of bupivacaine or pharmaceutically acceptable salt thereof over a period of 4 to 30 days, 4 to 10 days, or 5 to 7 days. The initial bolus dose provides immediate relief to the infection followed by continuous treatment reducing the infection. The drug depot may comprise a polymer and the polymer may comprise one or more of poly(lactide-co-glycolide), polylactide, polyglycolide, polyorthoester, D-lactide, D,L-lactide, poly(D,L-lactide), L-lactide, poly(D,L-lactide-co-caprolactone), poly(D,L-lactide-co-glycolide-co-caprolactone), polycaprolactone or a combination thereof. Bupivacaine may be in the form of a salt and/or in the form of a base. The polymer may be biodegradable. The drug depot may be a ribbon-like strip. The drug depot is capable of releasing about 40 to 90% of the bupivacaine or pharmaceutically acceptable salt thereof relative to a total amount of bupivacaine or pharmaceutically acceptable salt thereof loaded in the drug depot over the period of 4 to 10 days after the drug depot is administered to the target tissue site.

Having now generally described the invention, the same may be more readily understood through the following reference to the following examples, which are provided by way of illustration and are not intended to limit the present invention unless specified.

EXAMPLES

Example 1

A number of formulations of bupivacaine were prepared according to the following procedures:

Materials: Poly(D,L-lactide-co-caprolactone) having a 25:75 lactide to caprolactone molar ratio (25:75 DL-CL), an intrinsic viscosity of 0.8 dL/g and a molecular weight of 95 kDa was purchased from Lakeshore Biomaterials (Birmingham, Ala.). Poly(D,L-lactide-co-glycolide-co-caprolactone) having a 30:20:50 lactide to glycolide to caprolactone molar ratio (30:20:50 DL-G-CL), an intrinsic viscosity of 0.05 dL/g to 0.15 dL/g and a molecular weight of 10 kDa was purchased from Lakeshore Biomaterials (Birmingham, Ala.). Bupivacaine Base was purchased from Orgamol (Switzerland). Polyethylene glycol (PEG) having an average molecular weight of 300-400 g/mol was purchased from Spectrum Chemicals, n-methylpyrrolidone (NMP) having an average molecular weight of 99 g/mol was purchased from Fisher, and acetone was also purchased from Sigma-Aldrich.

Methods:

Preparation of bupivacaine base/25:75 DL-CL strip implant: The 25:75 DL-CL polymer was added to a glass vial and heated to either 100° C. (below drug melt temp) or 110° C. (above drug melt temp). Bupivacaine base was added to the melted polymer and mixed with a spatula until visually homogeneous. The resulting blend was removed from the glass vial and pressed into a thin film (0.4-0.6 mm thickness) using a Carver Press. The Carver Press was operated at 45° C. and 6000-8000 psi pressure. The thin film was cut to form a strip of the desired dimensions with a sharp blade. The dimensions of the strip were 9 mm in length, 0.4 to 1 mm in thickness and 1.5 to 3 mm in width.

Preparation of bupivacaine base/30:20:50 DL-G-CL injectable paste/gel formulation: The polymer (318 mg), PEG 300 (92 mg) and NMP (199 mg) were added to a glass vial and heated to 93° C. for approximately 10 minutes. The bupivacaine (911 mg) was added to the mixture and maintained at 93° C. for 20 minutes while being stirred/vortexed to get the drug to dissolve. Vail was removed from the heat and the mixture was stirred as it cooled to room temperature. The formulation was collected from the vial and added to a 1 mL syringe. The mixture was easily expelled from the syringe (no needle attached) when heated to 40° C.

In Vitro drug elution testing of bupivacaine base/25:75 DL-CL ribbon implant and Bupivacaine base/30:20:50 DL-G-CL injectable gel formulation: The purpose of this procedure was to measure the release of bupivacaine from a polymer strip and a gel formulation into a receiving fluid PBS buffer, pH 7.4. The in vitro release procedure consisted of placing a known mass of implant or gel into an apparatus containing the receiving fluid. The in vitro release apparatus consisted of a 60 ml glass bottle. A receiving fluid in the amount of 30 ml was added to each sample bottle. During the release study, the apparatus was placed in an incubator maintained at 37±2° C. At predetermined intervals, samples of the receiving fluid were removed and analyzed for bupivacaine concentration by HPLC.

Figure 5:
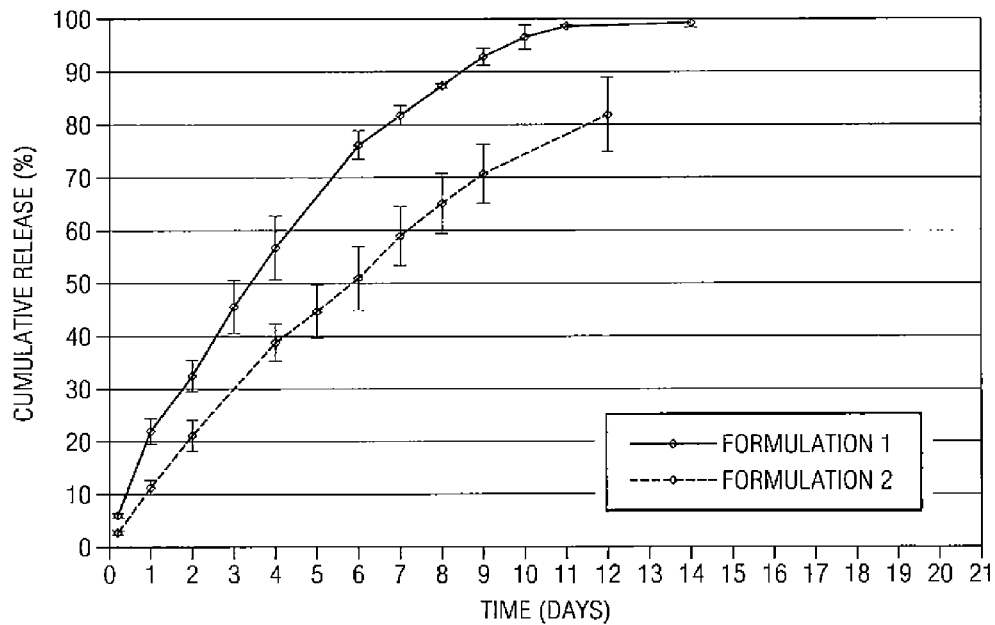
FIG. 5 is a graphic representation of the cumulative in vitro release profile for certain bupivacaine formulations.
Figure 6:
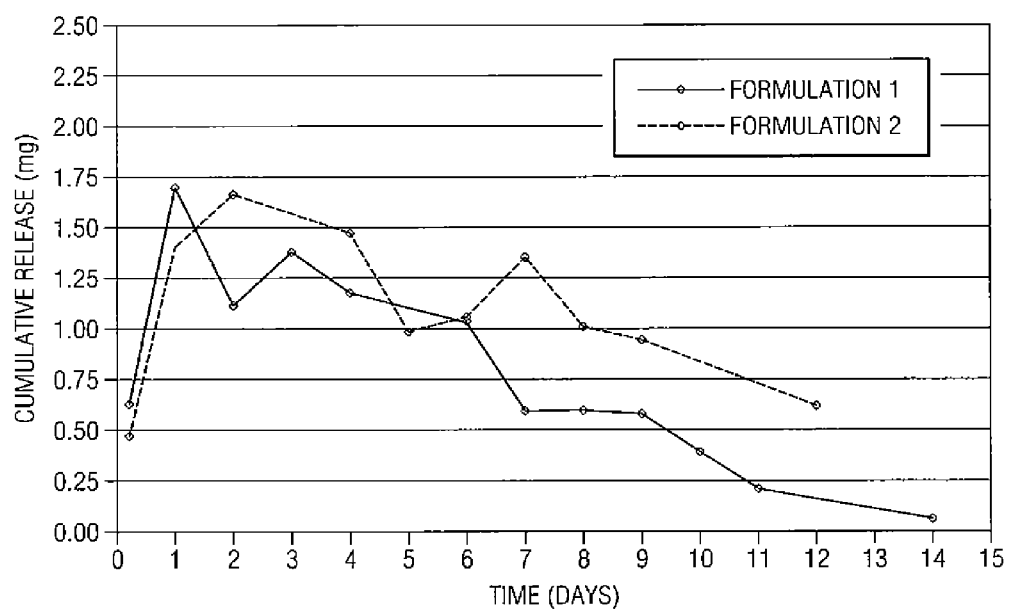
FIG. 6 is a graphic representation of the cumulative daily release profiles for the certain bupivacaine formulations illustrated in FIG. 5.

Elution profile: These formulations of bupivacaine were tested in Brennan rats to determine their in vitro elution. FIGS. 5 and 6 show the average cumulative release profiles of these bupivacaine formulations. Also, the results are summarized below in Table 1:

TABLE 1

| Formulation Number | Polymer | Active Wt. % of Bupivacaine | Excipient | Handling Property | In vitro Elution Profile |
|---|---|---|---|---|---|
| 1 | 2575 DL-CL 8E | 63% (bupivacaine base) | None | Malleable | Day 1 burst release of 22%. 97% eluted by day 10. |
| 2 | 30:20:50 DL-G-CL 1E | 60% (bupivacaine base) | 6% PEP 300, 13% NMP | Injectable Paste | Day 1 release of 12%, 75% of the drug eluted by day 10 |

DL-CL is an abbreviation for poly(DL-lactide-co-caprolactone) polymer.

For formulation 1, there was a concern that the co-polymer could take up to 6-8 months to fully degrade. No excipient was needed because the bupivacaine was melted before it was mixed with the polymer. The malleability was of sufficient flexibility to permit extrusion to a strip or ribbon dosage form.

For formulation 2, the degradation of the polymer was less than one month.

Example 2

A number of formulations of bupivacaine were prepared according to the following procedures:

Materials: Poly(D,L-lactide-co-glycolide) having a 50:50 lactide to glycolide molar ratio (PLGA 50501A), an intrinsic viscosity of 0.12 and acid end capped polymer chain ends was purchased from Lakeshore Biomaterials (Birmingham, Ala.). Bupivacaine Base was purchased from Orgamol (Switzerland). Bupivacaine HCl was purchased from Spectrum Chemicals (Gardena, Calif.). Methoxy polyethylene glycol (mPEG) having an average molecular weight of 550 was purchased from Sigma-Aldrich. Methanol and acetone was also purchased from Sigma-Aldrich.

Methods:

Preparation of spray dried bupivacaine base/PLGA50501A: Bupivacaine base and PLGA50501A were both dissolved in acetone to yield a 10% (w/w) solution. A mixture of 65.2% bupivacaine base solution and 34.8% PLGA50501A solution was spray dried in the Buchi Spray Dryer. The processing parameters were set as follows: inlet temp. (70° C.), aspirator (80%), nitrogen inlet (50 mm), spray flow rate (80 mL/hr) and ultrasonic generator (0.8 watts). The spray dried powder was collected and dried for an additional 24 hours at 30° C. and 15 mmHg vacuum.

Preparation of spray dried bupivacaine HCl: Bupivacaine HCl was dissolved in methanol to yield a 10% (w/w) solution and the solution was spray dried in the Buchi Spray Dryer. The processing parameters were set as follows: inlet temp. (70° C.), aspirator (80%), nitrogen inlet (50 mm), spray flow rate (80 mL/hr) and ultrasonic generator (0.8 watts). The spray dried powder was collected and dried for additional 24 hours at 70° C. and 15 mm Hg vacuum.

Preparation of melt extruded rods: Three formulations were prepared for melt extrusion. All three formulations contained PLGA50501A ground into powder using a Retsch (Retsch GmbH, Germany) rotor mill with an 80 micrometer sieve filter. The first such formulation contained 30% (w/w) ground PLGA50501A, 60% (w/w) spray dried bupivacaine HCl, and 10% (w/w) mPEG (60% bupivacaine HCl). The second formulation contained 90% (w/w) spray dried bupivacaine base/PLGA50501A and 10% (w/w) mPEG (60% bupivacaine base). The last formulation contained 90% (w/w) ground PLGA50501A and 10% (w/w) mPEG (vehicle polymer). The last formulation was not tested.

The first two formulations were dry mixed with a spatula prior to being feed into a Haake Mini-Lab twin screw extruder (Thermo Fischer Scientific, Waltham, Mass.). The extruder settings were as follows: 105° C. and 30 RPM for the 60% bupivacaine HCl formulation, and 85° C. and 30 RPM for the 60% bupivacaine base formulation. The first two formulations were extruded out of a 1.5 mm diameter die.

Strip preparation: Extruded formulations were pressed into sheets of a desired thickness using a Carver Laboratory Heat Press (Carver, Inc., Wabash, Ind.) set at 50° C. The sheets were cut by razor blades to form strips of the desired dimensions. The dimensions of each formulation were (length by width by height or L×W×H): 60% bupivacaine base (9 mm×3 mm×1 mm), and 60% bupivacaine HCl (9 mm×3 mm×1 mm).

In Vitro drug elution testing: Each strip formulation was tested in triplicate and placed in 20 mL scintillation vials for drug elution testing. The 60% bupivacaine HCl and 60% bupivacaine base strips (or ribbons) were incubated in 10 mL of phosphate buffer with 0.5% (w/w) sodium dodecyl sulfate pH 7.4 at 37° C. under mild agitation. At pre-selected times, the buffer was removed for analysis and replaced with fresh buffer medium. The drug content was quantified at 260 nm for bupivacaine by Molecular Devices SpectraMax M2 (Sunnyvale, Calif.) plate reader.

Figure 3:
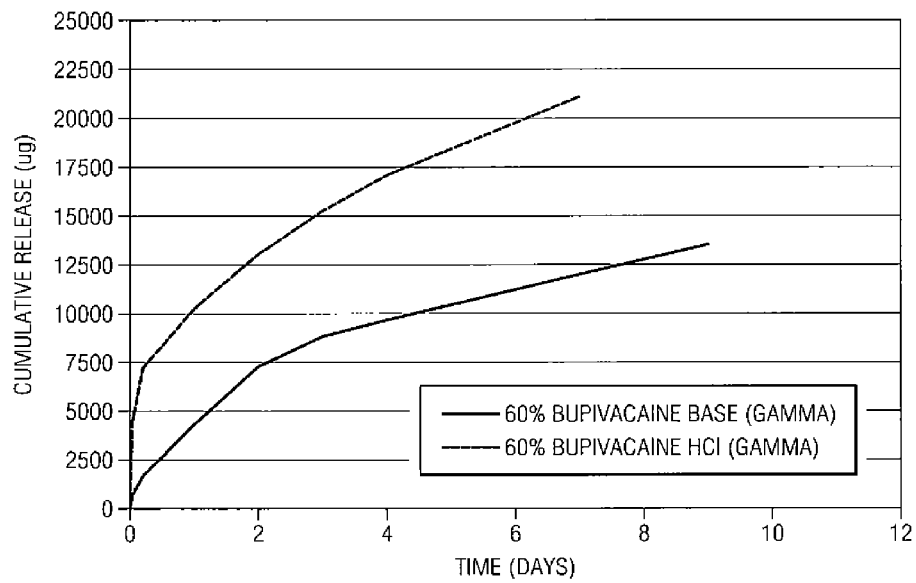
FIG. 3 is a graphic representation of a study of the cumulative release in ug of bupivacaine sterilized formulations.
Figure 4:
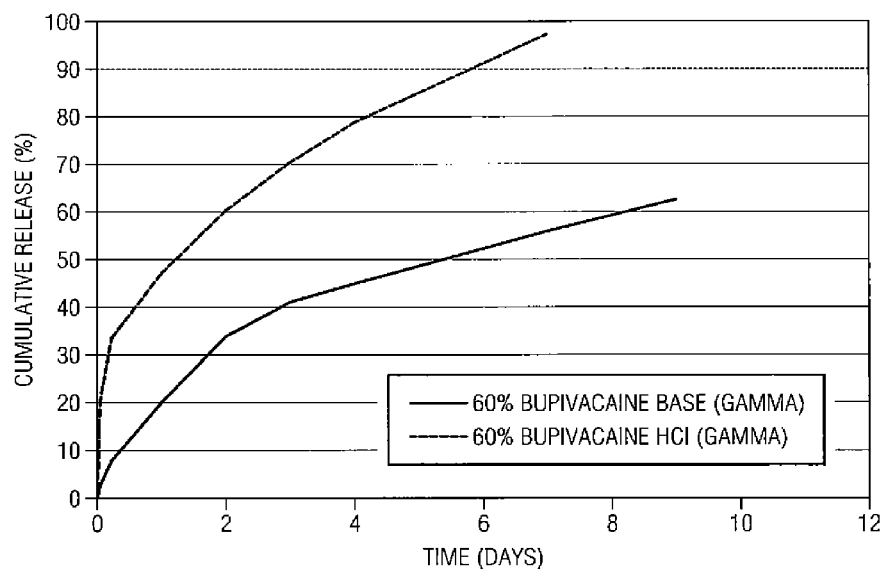
FIG. 4 is a graphic representation of a study of the percentage cumulative release of sterilized bupivacaine formulations.

Elution profile: These formulations of bupivacaine were tested in Brennan rats to determine the in vitro elution. FIGS. 3 and 4 show the release rate of the bupivacaine 3 formulation (labeled as Bupivacaine HCl in the figures) and the bupivacaine 4 formulation (labeled as Bupivacaine Base in the figures) from Table 2 in micrograms and percentages. The results are also summarized below in Table 2:

TABLE 2

| Formulation Number | Polymer (wt. %) | Active wt. % of Bupivacaine | Excipient (wt. %) | Handling Property | In vitro elution profile |
|---|---|---|---|---|---|
| bupivacaine 3 | 30% PLGA 50501 A | 60% (bupivacaine HCl) | 10% mPEG | Sticky, malleable | Day 1 release of 47%; by day 7, 100% released |
| bupivacaine 4 | 30% PLGA 50501 A | 60% (bupivacaine base) | 10% mPEG | Sticky, malleable | Day 1 release of 20%; by day 9, 70% released |
| bupivacaine 5 | PLA-C12 gel | 30% (bupivacaine base) | None | Injectable | Day 1 burst release of 30%; by day 10, 70% of the drug eluted |

For the bupivacaine 3 and 4 formulations, the polymer degraded in less than one month. The handling property was of a nature to enable a malleable and formable formulation product that could be extruded to a strip-like (ribbon) dosage form.

For the bupivacaine 5 formulation, the degradation of the polymer took at least a couple of months.

Example 3

A number of additional bupivacaine base formulations were prepared and their cumulative in vitro release profiles was measured.

Materials: Poly(D,L-lactide-co-caprolactone) having a 25:75 lactide to caprolactone molar ratio (25:75 DL-CL), an intrinsic viscosity of 0.8 dL/g and a molecular weight of 95 kDa was purchased from Lakeshore Biomaterials (Birmingham, Ala.). Poly(D,L-lactide-co-glycolide-co-caprolactone) having a 30:20:50 lactide to glycolide to caprolactone molar ratio (30:20:50 DL-G-CL), an intrinsic viscosity of 0.05 dL/g to 0.15 dL/g and a molecular weight of 10 kDa was purchased from Lakeshore Biomaterials (Birmingham, Ala.). Bupivacaine base was purchased from Orgamol (Switzerland). The PEG polymers having average molecular weights of 300, 1,500 and 8,000 were purchased from Spectrum Chemicals, n-methylpyrrolidone (NMP) having an average molecular weight of 99 g/mol was purchased from Fisher, and acetone was also purchased from Sigma-Aldrich. Labrosol consists of PEG-8 caprylic/capric glycerides was purchased from Gattefosse, USA (Paramus, N.J.). Trehalose having an average molecular weight of 324 g/mol was purchased from Sigma-Aldrich (St. Louis, Mo.).

Methods:

Preparation of bupivacaine base/DL-CL strips: The 10:90, 25:75 or 65:35 DL-CL polymer were each added to glass vials and heated to either 100° C. (below drug melt temp) or 110° C. (above drug melt temp). Bupivacaine base was added to the melted polymers and mixed with a spatula until visually homogeneous. The resulting blend was removed from the glass vial and pressed into a thin film (0.4-0.6 mm thickness) using a Carver Press. The Carver Press was operated at 45° C. and 6000-8000 psi pressure. The thin film was cut to form strips (ribbons) of the desired dimensions with a sharp blade. The dimensions of the implants were 9 mm in length, 1.5 to 3 mm in width and 0.5 to 1 mm in thickness.

In Vitro drug elution testing of bupivacaine base/25:75 DL-CL ribbons: The purpose of this procedure was to measure the release of bupivacaine from a polymer formulation into a receiving fluid PBS buffer, pH 7.4. The in vitro release procedure consisted of placing a known mass of implant or gel into an apparatus containing the receiving fluid. The in vitro release apparatus consisted of a 60 ml glass bottle. A receiving fluid in the amount of 30 ml was added to each sample bottle. During the release study, the apparatus was placed in an incubator maintained at 37±2° C. At predetermined intervals, samples of the receiving fluid were removed and analyzed for bupivacaine concentrations by HPLC. The drug loadings for these formulations are summarized in Table 3 below. In addition, Table 3 provides a description for each of these bupivacaine formulations.

TABLE 3

| Batch Number | Polymer | Molar Ratio of Polymers | Excipient | Drug Load (wt. %) | Description/Shape |
|---|---|---|---|---|---|
| 00180-25 | DL-CL | 10:90 | None | 62.16 | extruded, ribbon shaped |
| 00180-26 | 5050 4C PEG 1500 | — | None | 71.34 | extruded, ribbon shaped |
| 00180-27 | 5050 2C PEG 1500 | — | None | 58.96 | extruded, ribbon shaped |
| 00180-28 | DL-CL 8E | 25:75 | None | 53.83 | maleable, formable product |
| 00180-36 | DL-CL 8E | 25:75 | None | 70.88 | maleable, formable product |
| 00180-38 | DL-CL 8E | 25:75 | 100 mg NMP | 57.5 | maleable, formable product |
| 00180-39 | DL-CL 8E | 25:75 | None | 61.7 | maleable, formable product |
| 00180-40 | DL-CL 8E | 25:75 | None | 60.6 | maleable, formable product |
| 00180-53 | DL-CL 4A | 65:35 | None | 70 | very hard, not very formable product |
| 00180-54 | DL-CL 5A | 25:75 | None | 70 | brittle, crumbly, not formable product |
| 00180-55 | DL-CL 5A | 25:75 | 118 mg NMP | 65.92 | maleable, formable product- investigation |
| 00180-56 | DL-CL 4A | 65:35 | 118 mg NMP | 66.19 | of lower MW polymers with acid end |
| 00180-57 | DL-CL 5A | 25:75 | 20.5 mg NMP | 60.11 | group chemistry |
| 00180-58 | DL-CL 4A | 65:35 | 45.6 mg NMP | 58.37 | |
| 00180-79-01 | DL-CL 8E | 25:75 | 2% PEG 1500 | 62.69 | somewhat tacky, easily formable initially, after handling for a few minutes, the material becomes crumbly |
| 00180-79-02 | DL-CL 8E | 25:75 | 2% PEG 8000 | 61.9 | somewhat tacky, easily formable, holds together much better than PEG1500 formulation (180-79-01), does not crumble after prolonged handling |
| 00180-80-01 | DL-CL 8E | 25:75 | 2% trehalose, 4% NMP | 61.57 | easy to handle, smooth texture, formable |
| 00180-80-03 | DL-CL 8E | 25:75 | 2% CMC, 4 % NMP | 61.03 | tacky, easy to handle, formable |
| 00180-80-04 | DL-CL 8E | 25:75 | 4% labrosol | 58.91 | tacky, easy to handle, formable |
| 00180-80-05 | DL-CL 8E | 25:75 | 5% 5050 20 PEG 1500 | 60.49 | flaky and crumbly, did not hold together well |
| 00180-112 | DL-CL 8E | 25:75 | None | 62.03 | maleable, formable product |

Example 4

Several bupivacaine gel formulations were prepared.
Preparation of PLA Gel: Depolymerization of Polylactic Acid with Dodecanol Polylactic acid (intrinsic viscosity of 5.71 and weight of 15.0 grams), 4-dimethylaminopyridine (weight of 9.16 grams), and dodecanol (weight of 5.59 grams) were added into a 100 mL round bottom flask, charged, capped with a rubber septum and placed in an oil bath at 140° C. The materials were heated at that temperature for 30 minutes after everything was melted and was stirred freely with a magnetic stir bar. After cooling, 15 mL of tetrahydrofuran was added into the flask to dissolve the materials and precipitated by adding heptane. After decanting off the solvents, the material was dissolved in chloroform (30 mL) and washed with hydrochloride (1 molar, 20 mL, three times) and brined once. The solution was dried over anhydrous sodium sulfate. Yellow oil was obtained after solvent removal by rota-evaporation. (Mn about 800 g/mol by end group analysis by H-NMR)

Method of preparation of bupivacaine gel formulations: The formulations were prepared to contain 70% (w/w) PLA gel and 30% (w/w) spray dried bupivacaine. For each formulation, the two components were added to a 2 cc transfer cup and mixed in a Flacktek, Inc. Speedmixer DAC 150 FVZ for 2 minutes. The mixed formulations were each then back loaded into a 1 mL BD syringe with a 18G 1.5 inch blunt tip needle.

Figure 7:
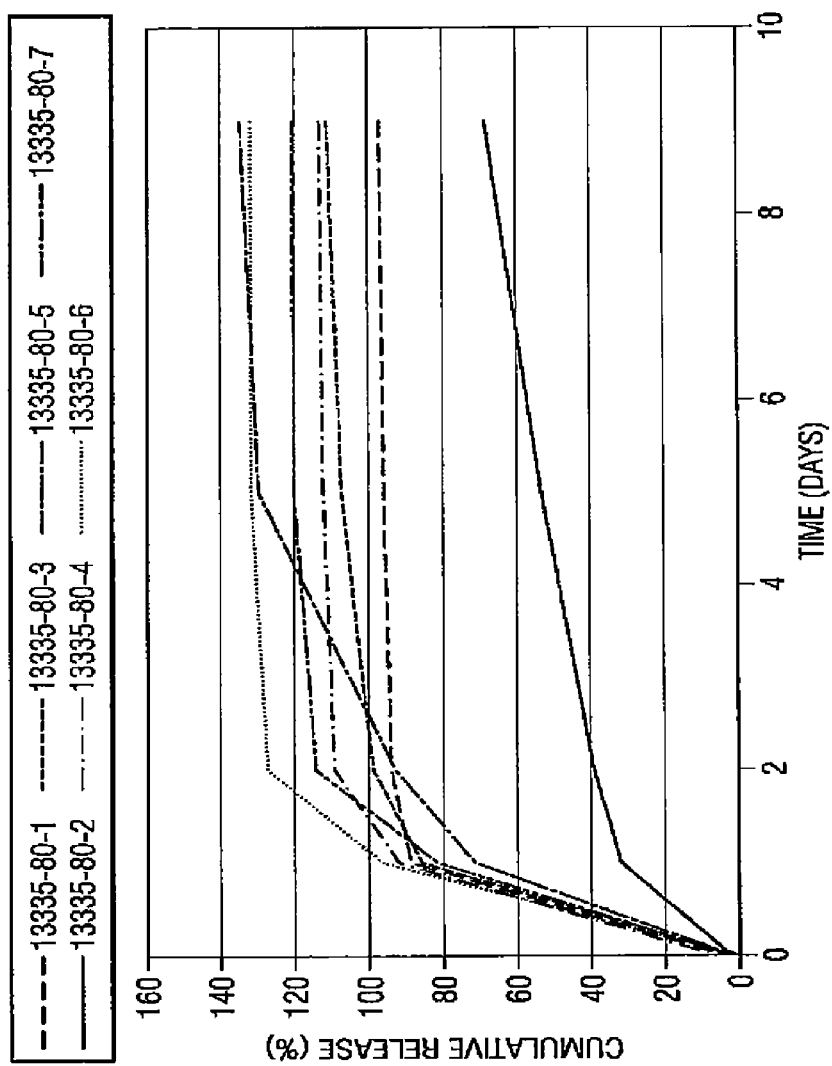
FIG. 7 is a graphic representation of the cumulative in vitro release profile for bupivacaine formulations from a study described in Example 4.
Figure 8:
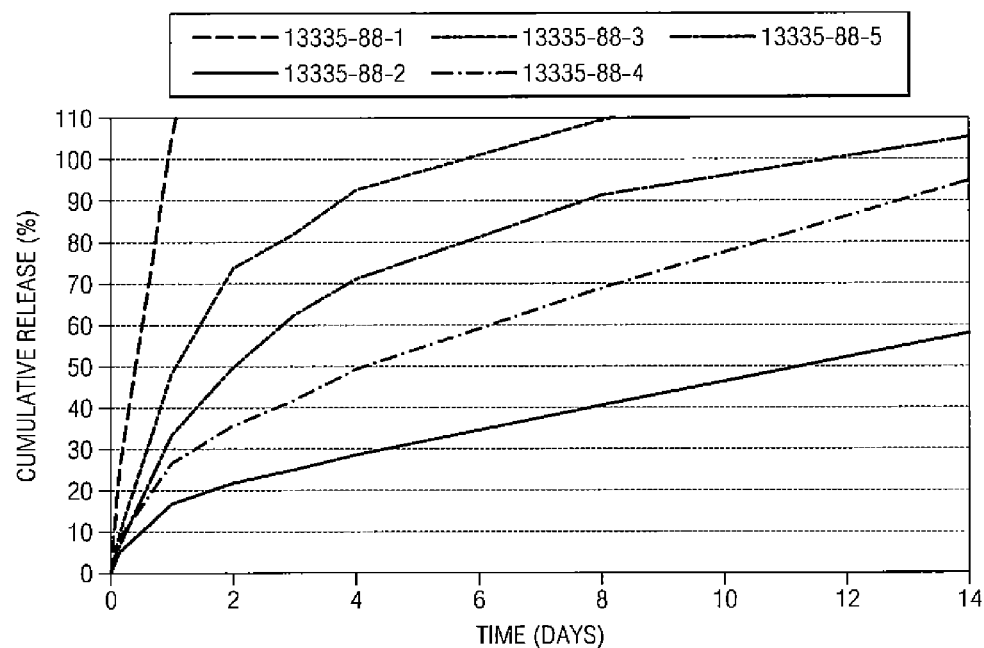
FIG. 8 is a graphic representation of the cumulative in vitro release profile for bupivacaine formulations from a study described in Example 4.
Figure 9:
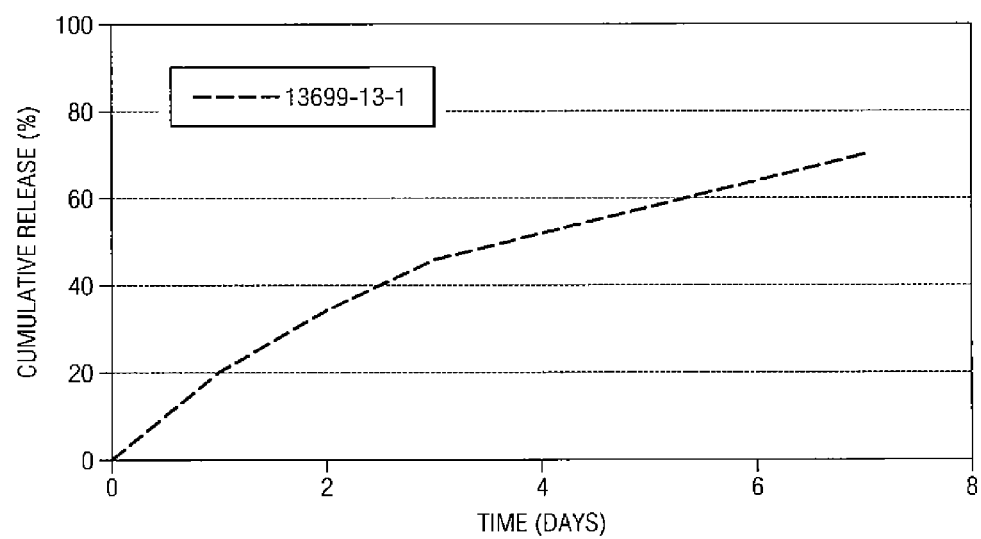
FIG. 9 is a graphic representation of the cumulative in vitro release profile for another bupivacaine formulation from a study described in Example 4.

In vitro drug elution testing: 100 uL of each of the gel formulations was injected in a 20 mL scintillation vial for drug elution testing. The formulations were each tested in triplicate and incubated in 10 mL of phosphate buffer with 0.5% (w/w) sodium dodecyl sulfate pH 7.4 at 37° C. under mild agitation. At pre-selected times, the buffer was removed for analysis and replaced with fresh buffer medium. The drug content was quantified for bupivacaine by a Molecular Devices SpectraMax M2 (Sunnyvale, Calif.) plate reader. The resulting formulations included 30% bupivacaine. FIGS. 7-9 show the in vitro cumulative percentage release of bupivacaine per day for the formulations which are listed below in Table 4.

TABLE 4

| Formulation ID | Drug Load (%) |
|---|---|
| 13335-80-1 | 30 |
| 13335-80-2 | 30 |
| 13335-80-3 | 30 |
| 13335-80-4 | 30 |
| 13335-80-5 | 30 |
| 13335-80-6 | 30 |
| 13335-80-7 | 30 |
| 13335-88-1 | 30 |
| 13335-88-2 | 30 |
| 13335-88-3 | 30 |
| 13335-88-4 | 30 |
| 13335-88-5 | 30 |
| 13699-13-1 | 30 |

Example 5

A number of formulations of bupivacaine were prepared according to the following procedures:

Materials: Poly(D,L-lactide-co-glycolide) having a 50:50 lactide to glycolide molar ratio (DLG 50501A), an intrinsic viscosity of 0.12 and acid end capped polymer chain ends was purchased from Lakeshore Biomaterials (Birmingham, Ala.). Bupivacaine base was purchased from Orgamol (Switzerland). Methoxy polyethylene glycol (mPEG) having an average molecular weight of 550 was purchased from Sigma-Aldrich. Methanol and acetone was also purchased from Sigma-Aldrich.

Methods:

Preparation of Spray Dried Bupivacaine Base/DLG 50501A: Bupivacaine base and DLG 50501A were both dissolved in acetone to yield a 10% (w/w) solution. A mixture of 65.2% bupivacaine base solution and 34.8% DLG 50501A solution was spray dried in the Buchi Spray Dryer. The processing parameters were set as follows: inlet temp. (70° C.), aspirator (80%), nitrogen inlet (50 mm), spray flow rate (80 mL/hr) and ultrasonic generator (0.8 watts). The spray dried powder was collected and dried for an additional 24 hours at 30° C. and 15 mm Hg vacuum.

Preparation of Melt Extruded Rods: Several formulations were prepared for melt extrusion. All formulations contained DLG 50501A ground into powder using a Retsch (Retsch GmbH, Germany) rotor mill with an 80 micrometer sieve filter. All formulations contained 60% (w/w) spray dried bupivacaine base/PLGA50501A.

The formulations were each dry mixed with a spatula prior to being fed into a Haake Mini-Lab twin screw extruder (Thermo Fischer Scientific, Waltham, Mass.). The extruder settings were as follows: 105° C. and 30 RPM for the 60% bupivacaine HCl formulation, and 85° C. and 30 RPM for the 60% bupivacaine base formulation. The formulations were extruded out of a 1.5 mm diameter die.

Strip Preparation: Extruded formulations were pressed into sheets of a desired thickness using a Carver Laboratory Heat Press (Carver, Inc., Wabash, Ind.) set at 50° C. The sheets were cut by razor blades to form strips of the desired dimensions. The dimensions of each of the formulations or strips were 9 mm in length by 3 mm in width by 1 mm in height.

Figure 10:
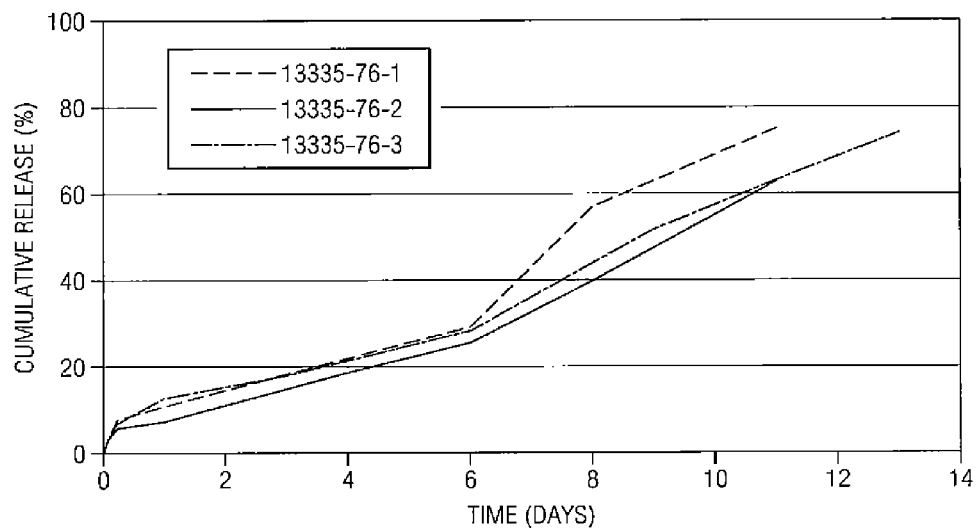
FIG. 10 is a graphic representation of the cumulative in vitro release profile for bupivacaine formulations from a study described in Example 5.
Figure 11:
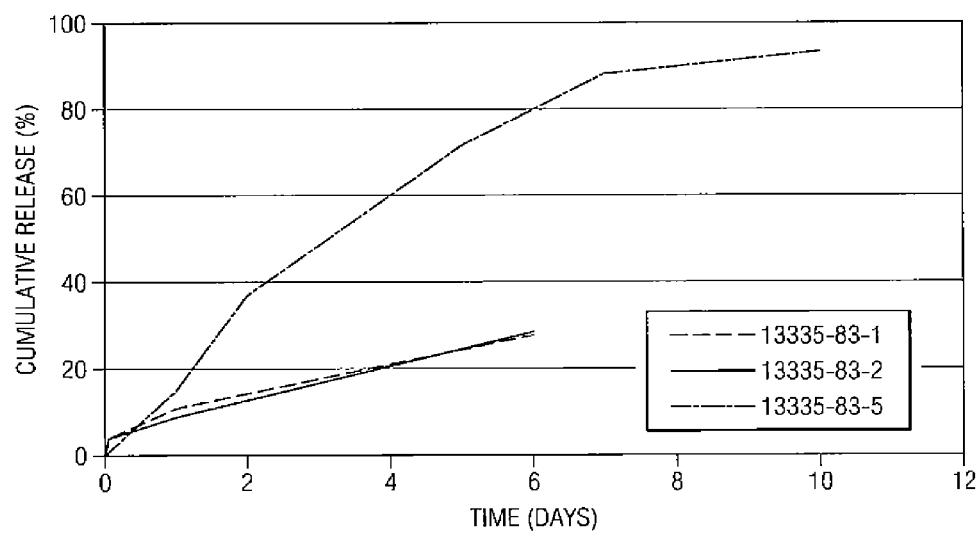
FIG. 11 is a graphic representation of the cumulative in vitro release profile for bupivacaine formulations from a study described in Example 5.

In Vitro Drug Elution Testing: Each strip formulation was tested in triplicate and placed in 20 mL scintillation vials for drug elution testing. The 60% bupivacaine base strips (or ribbons) were incubated in 10 mL of phosphate buffer with 0.5% (w/w) sodium dodecyl sulfate pH 7.4 at 37° C. under mild agitation. At pre-selected times, the buffer was removed for analysis and replaced with fresh buffer medium. The drug content was quantified at 260 nm for bupivacaine by Molecular Devices SpectraMax M2 (Sunnyvale, Calif.) plate reader. FIGS. 10 and 11 show the in vitro cumulative percentage release of bupivacaine per day for the formulations which are listed below in Table 5.

TABLE 5

| ID Number | Polymer | Drug Load (%) | Excipient | Ribbon Size (mm) (L × W × H) |
|---|---|---|---|---|
| 13335-76-1 | 5050 DLG 1A | 60 | 5% mPEG | 9 × 3 × 1 |
| 13335-76-2 | 5050 DLG 2A | 60 | 5% mPEG | 9 × 3 × 1 |
| 13335-76-3 | 5050 DLG 1A | 60 | 7% mPEG | 9 × 3 × 1 |
| 13335-83-1 | 5050 DLG 1A | 60 | 8% mPEG | 9 × 3 × 1 |
| 13335-83-2 | 5050 DLG 1A | 60 | 10% mPEG | 9 × 3 × 1 |
| 13335-83-5 | 5050 DLG 1A | 60 | 8% mPEG | 9 × 3 × 1 |

Example 6

Bupivacaine implants were prepared according to the procedure described in Example 5 above. The formulation used to prepare the implants is described below in Table 6. In particular, the formulation contained 50 wt. % bupivacaine base, 42 wt. % 5050DLG 1A, and 8 wt. % mPEG. The inherent viscosity of the 5050DLG was 0.05-0.15 and it had an acid end group.

TABLE 6

| Polymer | % Polymer | Drug Load (%) | Excipient | Ribbon Size (mm) (L × W × H) |
|---|---|---|---|---|
| 5050 DLG 1A | 42 | 50 | 8% mPEG | 9 × 3 × 1 |

Figure 12A:
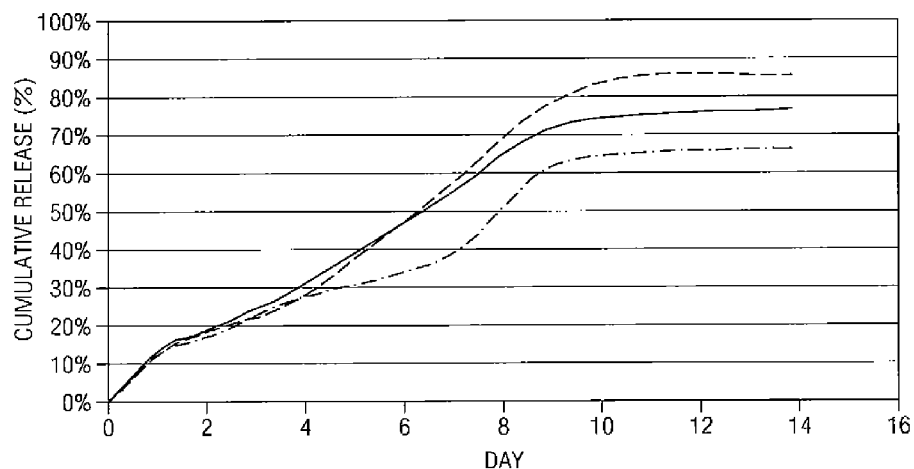
FIG. 12A is a graphic representation of the percentage cumulative release for three bupivacaine strips from a study described in Example 6.
Figure 12B:
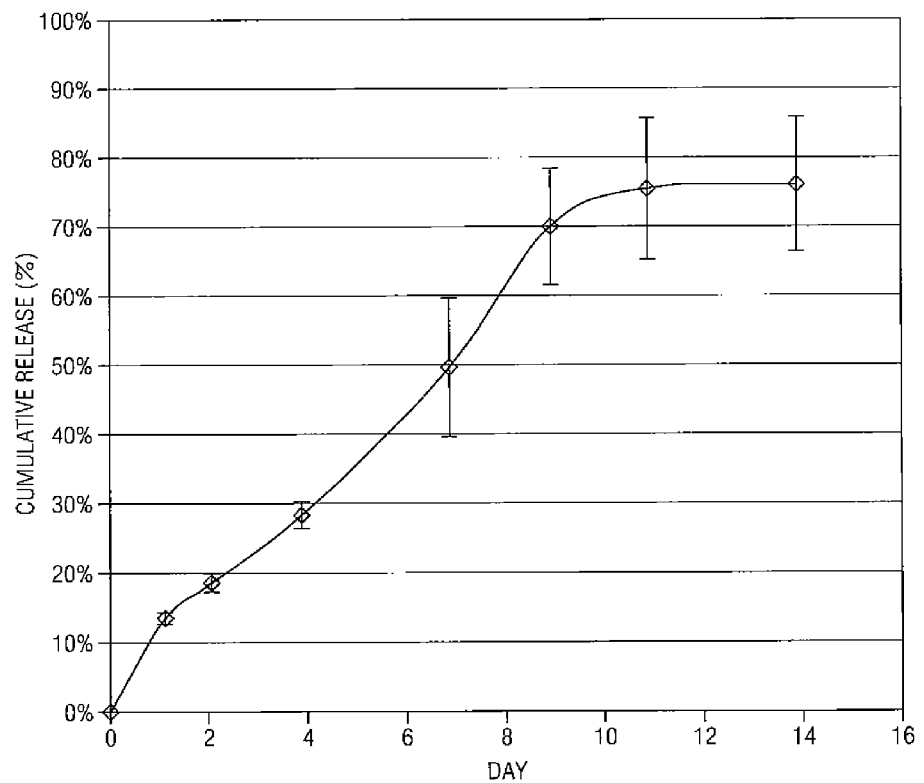
FIG. 12B is a graphic representation of the average percentage cumulative release for the bupivacaine strips shown in FIG. 12A.

The in vitro cumulative and daily release profile was tested before sterilization using three strip implants from the formulation described in Table 6. FIGS. 12A and 12B are in vitro graphic representations of the percentage cumulative release of three sterilized bupivacaine strips. As is readily apparent in these figures, each formulation released between 65% and 85% of the bupivacaine over 14 days with an average of 5%-10% of drug released every day. The average cumulative drug release of the three strips is shown in FIG. 12B, where 75% of the drug released in 14 days.

Figure 13A:
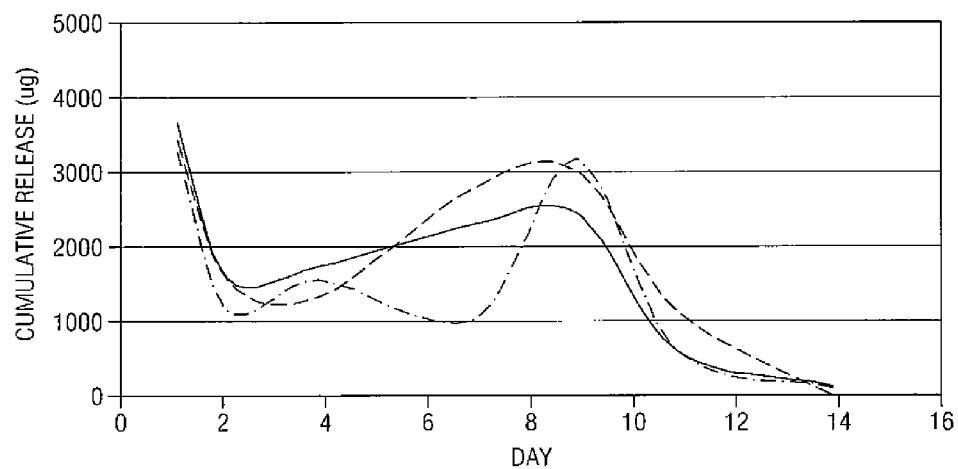
FIG. 13A is a graphic representation of the cumulative in vitro release in ug for the three bupivacaine strips described in Example 6.
Figure 13B:
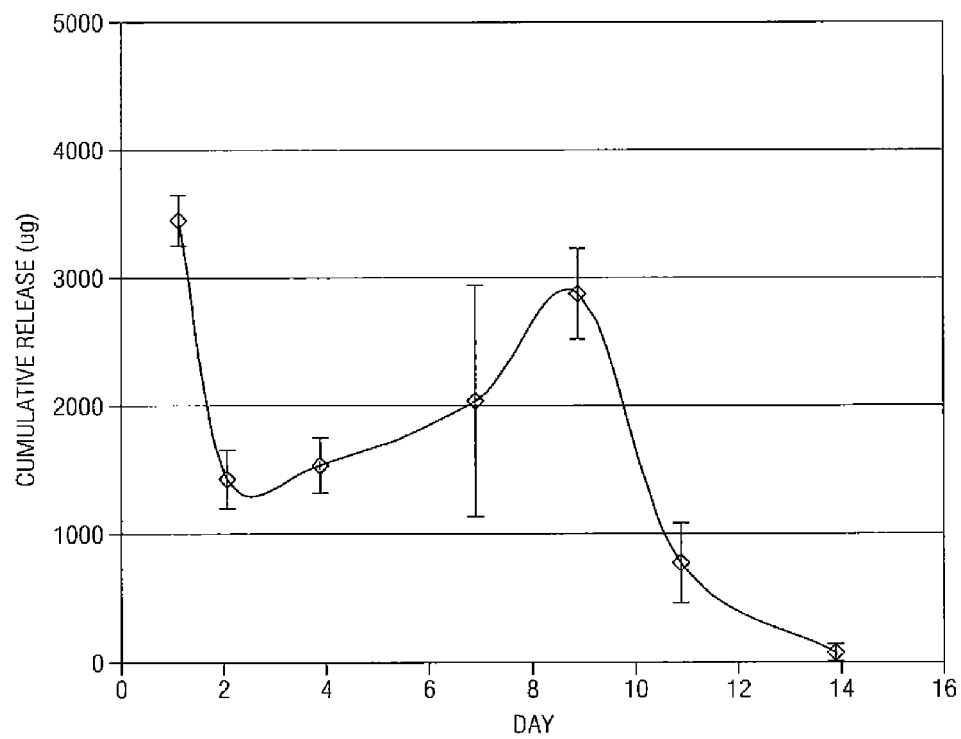
FIG. 13B is a graphic representation of the average cumulative in vitro release in ug for the bupivacaine strips shown in FIG. 13A.

FIGS. 13A and 13B are in vitro graphic representations of the daily release profile of the three sterilized bupivacaine strips and their cumulative average daily release in micrograms per day. As is readily apparent in these figures, each drug depot had an initial burst effect with a release of bupivacaine at a dose of about 3500 mcg within 2 days. After the two days, each drug depot released about 500-1000 mcg per day until the drug depot was exhausted at day 14.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. A drug depot useful for reducing, preventing or treating an infection in a patient in need of such treatment, the drug depot comprising a polymer and a therapeutically effective amount of a local anesthetic comprising bupivacaine or pharmaceutically acceptable salt thereof, the drug depot being administered at a site to reduce, prevent or treat an infection, wherein the drug depot is capable of releasing (i) a bolus dose of the local anesthetic or pharmaceutically acceptable salt thereof at the site from a layer, wherein between 15 and 25% of the bupivacaine is released within a 24 hour period and (ii) a sustained release dose of an effective amount of the local anesthetic or pharmaceutically acceptable salt thereof over a period of at least 4 days at the site, wherein the polymer comprises a particle size of about 10 μm to about 40 μm and is capable of degrading in less than 30 days after the drug depot is administered at the site.

2. A drug depot according to claim 1, wherein the polymer comprises one or more of poly(lactide-co-glycolide), polylactide, polyglycolide, polyorthoester, D-lactide, D,L-lactide, poly(D,L-lactide), L-lactide, poly(D,L-lactide-co-caprolactone), poly(D,L-lactide-co-glycolide-co-caprolactone), polycaprolactone or a combination thereof.

3. A drug depot according to claim 1, wherein the local anesthetic is released in an amount between 50 and 800 mg per day for a period of 4 to 10 days.

4. A drug depot according to claim 1, wherein the local anesthetic is present in an amount of about 30 to about 90 wt. % of the drug depot and the polymer is present in an amount of about 10 to about 80 wt. % of the drug depot, and the drug depot further comprises about 0.5 to about 20 wt. % of an excipient.

5. A drug depot for reducing, preventing or treating an infection in a patient in need of such treatment, the drug depot comprising bupivacaine or a pharmaceutically acceptable salt thereof in an amount from about 30 wt. % to about 90 wt. % of the drug depot, and at least one biodegradable material, wherein the drug depot is capable of releasing the bupivacaine or pharmaceutically acceptable salt thereof over a period of at least 4 days and the drug depot comprises a layer that releases between 15 and 25% of the bupivacaine within a 24 hour period, wherein the polymer comprises a particle size of about 10 μm to about 40 μm and is capable of degrading in less than 30 days after the drug depot is administered at the site.

6. A drug depot according to claim 5, wherein the at least one biodegradable material comprises one or more of poly(lactide-co-glycolide), polylactide, polyglycolide, polyorthoester, D-lactide, D,L-lactide, poly(D,L-lactide), L-lactide, poly(D,L-lactide-caprolactone), poly(D,L-lactide-co-glycolide-co-caprolactone), polycaprolactone or a combination thereof.

7. A drug depot according to claim 5, wherein the drug depot releases: (i) a bolus dose of the bupivacaine; and (ii) an effective amount of the bupivacaine over a period of at least four days.

8. A drug depot useful for reducing, preventing or treating an infection in a patient in need of such treatment, the drug depot comprising a therapeutically effective amount of bupivacaine or pharmaceutically acceptable salt thereof and a polymer; wherein the drug depot is administered at a target site to reduce, prevent or treat an infection, and the drug depot is capable of releasing (i) 30% of the bupivacaine or pharmaceutically acceptable salt thereof relative to a total amount of the bupivacaine or pharmaceutically acceptable salt thereof loaded in the drug depot over a first period of up to 24 hours from a first layer and (ii) about 50% to about 98% of the bupivacaine or pharmaceutically acceptable salt thereof relative to a total amount of the bupivacaine or pharmaceutically acceptable salt thereof loaded in the drug depot over a subsequent period of up to 3 to 10 days, wherein the polymer comprises a particle size of about 10 μm to about 40 μm and is capable of degrading in less than 30 days after the drug depot is administered at the site.

9. A drug depot according to claim 8, wherein the polymer comprises one or more of poly(lactide-co-glycolide), polylactide, polyglycolide, polyorthoester, D-lactide, D,L-lactide, poly(D,L-lactide), L-lactide, poly(D,L-lactide-co-caprolactone), poly(D,L-lactide-co-glycolide-co-caprolactone), polycaprolactone or a combination thereof.

10. A drug depot according to claim 8, wherein the polymer comprises about 15% to about 55% of the total weight of the drug depot.

11. A drug depot according to claim 8, wherein the drug depot is capable of releasing between 50 and 800 mg/day of bupivacaine or pharmaceutically acceptable salt thereof.

12. A drug depot according to claim 1, wherein 25% of the bupivacaine is released within a 24 hour period.

13. A drug depot according to claim 1, wherein the bupivacaine comprises a bupivacaine base.

14. A drug depot according to claim 1, wherein the drug depot further comprises trehalose.

* * * * *